(12) United States Patent
Frazer et al.

(10) Patent No.: US 6,891,031 B2
(45) Date of Patent: May 10, 2005

(54) COORDINATE CYTOKINE REGULATORY SEQUENCES

(75) Inventors: Kelly A. Frazer, San Mateo, CA (US); Edward M. Rubin, Berkeley, CA (US); Gabriela G. Loots, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/789,529

(22) Filed: Feb. 20, 2001

(65) Prior Publication Data

US 2002/0132290 A1 Sep. 19, 2002

Related U.S. Application Data

(60) Provisional application No. 60/183,657, filed on Feb. 18, 2000.

(51) Int. Cl.[7] .......................... C07H 21/04; C12N 15/63
(52) U.S. Cl. ................... 536/24.1; 435/320.1; 435/474; 424/85.1
(58) Field of Search ...................... 536/24.1; 435/320.1, 435/471; 424/85.1

(56) References Cited

U.S. PATENT DOCUMENTS 5,776,776 A    7/1998   Ordahl et al.

OTHER PUBLICATIONS

Cretu et al. Identificationand functional analysis of evolutionarily conserved non–coding sequences in the human 5q31 cytokine cluster region. functional genomics, abstracts 1999.*
D. Symula, et al., "Functional screening of an asthma QTL in YAC transgenic mice," Nature Genetics, vol. 23, pp. 241–244 (Oct. 1999).
D. A. Lacy, et al., "Faithful Expression of the Human 5q31 Cytokine Cluster in Transgenic Mice," The Journal of Immunology, (2000), vol. 164, pp. 4569–4574.
G. Cretu, et al., "Identification and Functional Analysis of Evolutionarily Conserved Non–Coding Sequences in the Human 5q31 Cytokine Cluster Region," Genomics Abstracts 1999, pp. 1–2.
G.G. Loots, et al., "Identification of a Coordinate Regulator if Interleukins 4, 13, and 5 by Cross–Species Sequence Comparisons," Science, (Apr. 7, 2000), pp. 136–140, vol. 288.
K. Murphy, et al., Science, (Jul. 5, 2000), vol. 288, No. 5475, p. 2319(a), web access.
q13;q23), PNAS, (Dec. 7, 1999), pp. 14535–14540, vol. 96, No. 25.
K. A. Frazer, et al., "Computational and Biological Analysis of 680 kb of DNA Sequence from the Human 5q31 Cytokine Gene Cluster Region," Genome Research, (1997), vol. 7, pp. 495–512.

C. S. Osborne, et al., "Transcriptional Regulation of Mouse Granulocyte–Macrophage Colony–Stimulating Factor/IL–3 Locus," The Journal of Immunolgy, (1995), vol. 155, pp. 226–235.
I. Dubchak, et al., "Active Conservation of Noncoding Sequences Revealed by Three–Way Species Comparisons," Genome Research, (2000), vol. 10, pp. 1304–1306.
A. K. Abbas, et al., "Functional diversity of helper T lymphoctes," Nature, (Oct. 31, 1996), vol. 383, pp. 787–793).
S. E. Daniels, et al., "A genome–wide search for quantitative trait loci underlying asthma," Nature, (Sep. 19, 1996), vol. 383, pp. 247–250.
D. S. Postma, et al., "Genetic Susceptibilty to Asthma—Bronchial Hyperresponsiveness Coinherited with a Major Gene for Atopy," N Engl J Med, (Oct. 5, 1995), vol. 333, pp. 894–900.
N. Takemoto, et al., "$T_h2$–specific DNase I–hypersensitive sites in the murine IL–13 and IL–4 intergenic region," International Immunology, (1998), Vo. 10, No. 12, pp. 1981–1985.
S. Agarwal, et al., "Modulation of Chromatin Structure Regulates Cytokine Gene Expression during T. Cell Differentiation," Immunity, (Dec. 1998), vol. 9, pp. 765–775.
Q. Li, et al., "Locus Control Regions Coming of Age at a Decade Plus," TIG, (Oct. 1999), vol. 15, No. 10, pp. 403–408.
R. C. Hardison, "Long Human–Mouse Sequence Alignments Reveal Novel Regulatory Elements: A Reason to Sequence the Mouse Genome," Genome Research, (1997), vol. 7, pp. 959–966.
E.M. Rubin, "Identification and Functional Analysis of Human–Mouse Conserved Non–Coding Sequences in the Human 5Q31 Cytokine Cluster Region," Genome Sequencing and Biology, (May 19, 1999).
Nucleotide Sequence Listing Accession No. AC004039 "Homo Sapiens chromosome 5, P1 clone 876h9, P1 5116 (LBNL H11), complete sequence" Version: AC004039.1; GI:2811101 (Jan. 27, 1998), Connoly et al.
Nucleotide Sequence Listing Accession No. AC004628 "Homo Sapiens chromosome 5, P1 clone 722G11 (LBNL H24), complete sequence" Version: AC004628.1; GI:3093424 (Apr. 29, 1998), Kimmerly et al.
Nucleotide Sequence Listing Accession No. AL645741 "Mouse DNA sequence from clone RP23–239O19 on chromosome 11, complete sequence" Version: AL645741.15; GI:212111994 (May 22, 2002), Dunn, M.

* cited by examiner

Primary Examiner—Janet Andres
Assistant Examiner—Fozia Hamud
(74) Attorney, Agent, or Firm—Townsend and Townsend and Crew LLP

(57) ABSTRACT

The present invention provides CNS sequences that regulate the cytokine gene expression, expression cassettes and vectors comprising or lacking the CNS sequences, host cells and non-human transgenic animals comprising the CNS sequences or lacking the CNS sequences. The present invention also provides methods for identifying compounds that modulate the functions of CNS sequences as well as methods for diagnosing defects in the CNS sequences of patients.

40 Claims, 4 Drawing Sheets

Fig. 2

Table 1. Cross-species sequence analysis of 15 conserved noncoding elements. Human and mouse sequence alignments of each element were inspected, and primer pairs were chosen from the most conserved regions. Hence, for each CNS, the size of the PCR amplified product(s) is smaller than the size of the element indicated in Fig. 1. Numbers in parentheses are percent identity. Dashes indicate that PCR did not amplify a product.

| Conserved noncoding sequence | Product base-pair size | | | | | | | | |
|---|---|---|---|---|---|---|---|---|---|
| | Human | Cow | Dog | Pig | Rabbit | Rat | Mouse | Chicken | Fugu |
| CNS-1  | 224 | 220 (86) | 218 (80) | 229* | 200 (72) | 214 (75) | 214 (76) | 266* | 155* |
| CNS-2  | 104 | 104 (90) | 105 (93) | 104 (89) | 101 (90) | 105 (85) | 104 (85) | 192* | 245* |
| CNS-3  | 131 | —  | —  | —  | —  | —  | 131 (73) | —  | —  |
| CNS-4  | 77  | 77 (88)  | —  | —  | —  | 77 (87)  | 77 (87)  | —  | —  |
| CNS-5  | 157 | —  | 157 (82) | —  | —  | 159 (84) | 159 (81) | —  | —  |
| CNS-6  | 148 | —  | —  | —  | —  | —  | 139 (87) | —  | —  |
| CNS-8  | 122 | —  | —  | —  | —  | —  | 122 (79) | —  | —  |
| CNS-9  | 124 | 125 (88) | 125 (91) | 125 (88) | 125 (92) | 124 (86) | 124 (86) | 120* | 111* |
| CNS-10 | 213 | 214 (82) | —  | 210 (84) | 209 (83) | 211 (79) | 211 (77) | —  | —  |
| CNS-11 | 120 | —  | 119 (89) | 119 (90) | 120 (83) | 119 (80) | 119 (79) | —  | —  |
| CNS-12 | 200 | —  | —  | —  | —  | 194† | 194 (78) | —  | —  |
| CNS-13 | 314 | 315 (73) | 295* | 317 (75) | —  | 324 (67) | 327 (68) | —  | 473* |
| CNS-14 | 128 | —  | —  | —  | —  | —  | 128 (60) | —  | —  |
| CNS-15 | 127 | 125 (90) | 125 (91) | 125 (90) | —  | 127 (86) | 127 (86) | —  | 88* |
| CNS-16 | 109 | 109 (74) | —  | —  | 109 (84) | 111 (83) | 109 (80) | —  | —  |

*Only primer sequences were conserved. †Amplified PCR product was not sequenced.

A
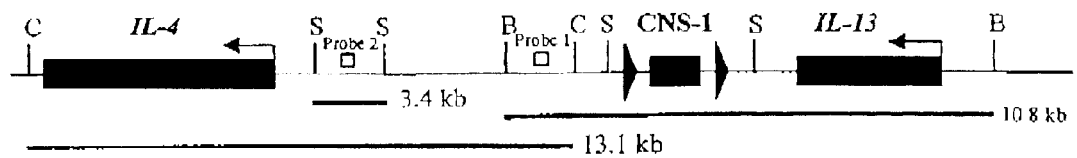
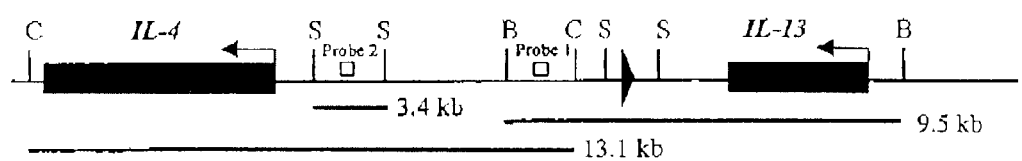
B
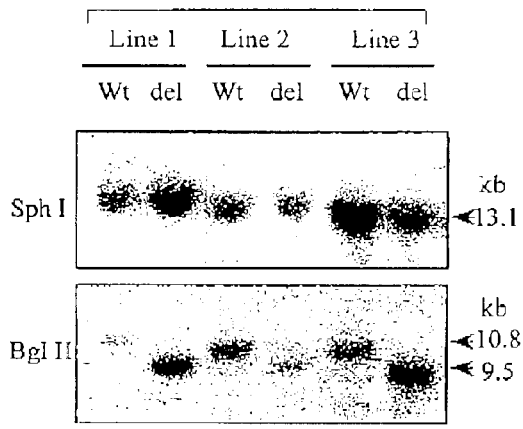
C
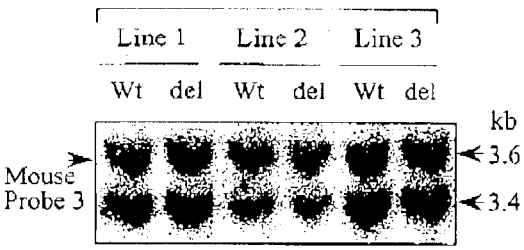
FIGURE 3

SEQUENCE LISTING

<160> NUMBER OF SEQ ID NOS: 90

<210> SEQ ID NO 1
<211> LENGTH: 445
<212> TYPE: DNA
<213> ORGANISM: Homo sapiens
<220> FEATURE:
<223> OTHER INFORMATION: human CNS-1

<400> SEQUENCE: 1

```
cttgagggtt tggggaaatg gtgtccagcc cccgcacagt tgtccacagt gatgcagaga    60
gtggagctga cgagagttgc tatatttaat tttggtgcct gcgtcacctc tgaccacaca   120
gcagcgtctg cccaggcagg cagcacatgg ctgggggtgt ttctgaacga cgctgtgaga   180
gaatcacttt ccccaagaaa aggtatagca gaggggaagg gagagacagc aacagaaagt   240
gaggtcgtaa gtagaaaatt gcttctggga tttcaaatgg ctttgtcatg gggccctccc   300
ttgctgccga gaaatcagtt gatctgggaa agtttgttgc aaaccttgc cctcttgctt   360 ttgggtggag ctgagaaatg aatgaagata atggggcttt atgagtgtgg gggagggtag   420
ctgaggagac agccaccagt cctga                                        445
```

<210> SEQ ID NO 2
<211> LENGTH: 368
<212> TYPE: DNA
<213> ORGANISM: Homo sapiens
<220> FEATURE:
<223> OTHER INFORMATION: human CNS-2

<400> SEQUENCE: 2

```
atgtgtggga aaatgattac gaagaggcta cttcaaaaag aacctgtttc ctctcagcat    60
ttatcttggg cttcctgtga cccaatcttc aagtgacttt tatcaacgtt atcagaagat   120
cagattgtct cacccaaaca cgtttatggc tctgactaaa gaatatgaca gatcagatat   180
tcctctccac ctgctcccct cccccatccc ttttagagg gctggggaaa tttagttt     240 taatcaaagg ctttatttct ccagttgtgc aaaggaattt aactgggact ttacaactga   300
ataaagtatt tctcagagtc gatactaatc ttagcaagag gatattgcct aacccaacct   360
aaaagcag                                                            368
```

<210> SEQ ID NO 3
<211> LENGTH: 150
<212> TYPE: DNA
<213> ORGANISM: Homo sapiens
<220> FEATURE:
<223> OTHER INFORMATION: human CNS-3

<400> SEQUENCE: 3

```
ccttcgaggc cacacccagt ggctcagggc acgatgccca ggccttctgt atgcagccag    60
gtctgtccaa ggtcaggaga agtcactgtg ctctttcctc aatgggcagg cagggctggc   120
aggctccagc aggagcagac acccttggga                                   150
```

<210> SEQ ID NO 4
<211> LENGTH: 218
<212> TYPE: DNA
<213> ORGANISM: Homo sapiens
<220> FEATURE:
<223> OTHER INFORMATION: human CNS-4

```
<400> SEQUENCE: 4
tggaaaaggc cccacctaag gctctaggac cagcagtccc tgagaagtag ctgtgtgtag    60
gattaagaca agctgactgc ggagagctgt gacattgggc attcaagcat gaagcattgt   120
tggcccagag agggtgcaca agcattctcc ctcagagaac catggtgttc cagagccaga   180
gagagatgga gagcttccac aatccttgtg aagatctg                           218

<210> SEQ ID NO 5
<211> LENGTH: 123
<212> TYPE: DNA
<213> ORGANISM: Homo sapiens
<220> FEATURE:
<223> OTHER INFORMATION: human CNS-5

<400> SEQUENCE: 5
cccctagagg caggcagggt gatgactgaa gcatcaggcc tgtggtttct gtaacaggaa    60
gtgatttaga tgctgaaagc taattttaga tgaaatgata tggggttttt aaagaatctt   120
tca                                                                 123

<210> SEQ ID NO 6
<211> LENGTH: 118
<212> TYPE: DNA
<213> ORGANISM: Homo sapiens
<220> FEATURE:
<223> OTHER INFORMATION: human CNS-6

<400> SEQUENCE: 6
gccagaaaac cgctgtcctg actcagtgtc ttgccccacc ctggcctctg gcccagattc    60
tggaggcctt agtcaggggg tggggtctg tttgcccaga gctggggttt ccctatag     118

<210> SEQ ID NO 7
<211> LENGTH: 162
<212> TYPE: DNA
<213> ORGANISM: Homo sapiens
<220> FEATURE:
<223> OTHER INFORMATION: human CNS-7

<400> SEQUENCE: 7
tggataggag ccagggcctc catcaggaga gcttggggct gccccaggcc taactggagg    60
aagtgtgaca cattcccaga gagctgggct tccctccctc ctgcagcttc ctttgagatg   120
gttcccgaat ccgttaagtg ggaaaaagag ctggcagctg tg                      162

<210> SEQ ID NO 8
<211> LENGTH: 181
<212> TYPE: DNA
<213> ORGANISM: Homo sapiens
<220> FEATURE:
<223> OTHER INFORMATION: human CNS-8

<400> SEQUENCE: 8
caaactgata ctgcacttgg tttcaccaag ctgaagtaaa ctctgtaaaa gatgaggaag    60
tgactttagc atttgcaaat atttcagaat gcctttgtgc cagcaaaggt caaacaacga   120
tcagaattgc atggattcca agtatactt ttgggaaata agagactcag agaagcatta   180
c                                                                   181
```

```
<210> SEQ ID NO 9
<211> LENGTH: 157
<212> TYPE: DNA
<213> ORGANISM: Homo sapiens
<220> FEATURE:
<223> OTHER INFORMATION: human CNS-9

<400> SEQUENCE: 9
agtgactgat gtttgcacct ggtaattgag gtcaggttgc ttctcttaag tcacatgatt     60
tgcgtcaaag caggaaggtg tcggggccac ttgttgcaaa gagaccagga ggcgatccca    120
gcaacgctgc aaaccagctt tggcagcaaa ggctgtg                             157

<210> SEQ ID NO 10
<211> LENGTH: 244
<212> TYPE: DNA
<213> ORGANISM: Homo sapiens
<220> FEATURE:
<223> OTHER INFORMATION: human CNS-10

<400> SEQUENCE: 10
ggctaactgc ggcaggatga ctcagccagc acaaggggta cattcaggct tctgtgggcg     60
gaggaagttt cttgaaagca gtggtggctg ggatgctgcc agctctattg agctagggga    120
gttctggtca gagagggcgt gaggccaaga aattgtgact ctcccagtca cctttacatg    180
cattatctca ttaatcctga aggcaagccc atttcctaga tcaggaaacg gaggtccaga    240
gaag                                                                244

<210> SEQ ID NO 11
<211> LENGTH: 151
<212> TYPE: DNA
<213> ORGANISM: Homo sapiens
<220> FEATURE:
<223> OTHER INFORMATION: human CNS-11

<400> SEQUENCE: 11
aactggaaaa ttttggcaaa atgtcacaat gttctagtgt cctaaaagct caacatactg     60
gggcttagga actttccagg ggagagacaa taagaccaca gtctgcacag agccttctgt    120
gtggctgtga cagcgaggac aaaaacaatc a                                   151

<210> SEQ ID NO 12
<211> LENGTH: 223
<212> TYPE: DNA
<213> ORGANISM: Homo sapiens
<220> FEATURE:
<223> OTHER INFORMATION: human CNS-12

<400> SEQUENCE: 12
aggaaaaagc aaccaatctc cacattttct tgcctttgtt ttgtttatca agggaaatct     60
tgttctcatt tttatggcaa atgtttatga ctttgaacca ggaacttgcc tgccttgtat    120
ttctcttgca ctgctttatc ctgtttcctg agttgctagt tttgagattg tgtaagcgtt    180
gttagaggat ttccagcaac atcaaagggc agagacactg cct                      223

<210> SEQ ID NO 13
<211> LENGTH: 170
<212> TYPE: DNA
<213> ORGANISM: Homo sapiens
<220> FEATURE:
<223> OTHER INFORMATION: human CNS-13
```

```
<400> SEQUENCE: 13
gcaacaaaac tggtcctgga gccgtggttg gttcagcaga acacacaggg gagggcgtgc      60
ctgtggcaaa gggcgtttcc cagctctagt tttgtgccat tcaatccctc aacaaacact     120
tattgagtgc ctgctctatg tccagcccag acctggtcaa ctaaccttgg                170

<210> SEQ ID NO 14
<211> LENGTH: 213
<212> TYPE: DNA
<213> ORGANISM: Homo sapiens
<220> FEATURE:
<223> OTHER INFORMATION: human CNS-14

<400> SEQUENCE: 14
ctatgataga atttaagcac tcagaacttt gtgtatttaa ggtactaaaa taacaagtta      60
tttggcaatt cccctgaaac tttcacctaa gccctaactt cctcagtgta acataaaggt     120
gtcaggggga atcagagaga acgctctcat attctctggg aagagaaagc tcctgccaga     180
actcagcttc ttttctgaga ataccatttt aag                                  213

<210> SEQ ID NO 15
<211> LENGTH: 203
<212> TYPE: DNA
<213> ORGANISM: Homo sapiens
<220> FEATURE:
<223> OTHER INFORMATION: human CNS-15

<400> SEQUENCE: 15
cggcagcagt gacagccaat gggcagcaaa gcttgttgct aaggtcactg tgagccttat      60
ttggtgacac agggctgacc ctgcattcac ctctgagaac cctgggaaac gccaaccaca     120
gatgtgaaat atgaacatct caaaaccaca actgcatttc ctttgagaaa agattcggct     180
gtcctcctct ccagcctgcc tcc                                             203

<210> SEQ ID NO 16
<211> LENGTH: 310
<212> TYPE: DNA
<213> ORGANISM: Homo sapiens
<220> FEATURE:
<223> OTHER INFORMATION: human CNS-16

<400> SEQUENCE: 16
gagactacgt gggtgcagct ctgaggaatg agtcggttga gggaatctag ggtctcctca      60
tttcctaaga aggcctccct ttttcactct gccctcccac atccttggga gggtctgaga     120
ctggaagcaa ggccttggct gatgtgtggc cacgctggct gatagtgtgc agagggctag     180
gaggtgtgtc cctggctcct ggggtctgtc aagagttac tattatgcag atggaagttg     240
gcaggaaaag ctgtgatgca agtacatgca agcccagcag agtgctggag tgagagttaa     300
acttcgggaa                                                            310

<210> SEQ ID NO 17
<211> LENGTH: 463
<212> TYPE: DNA
<213> ORGANISM: Mus musculus
<220> FEATURE:
<223> OTHER INFORMATION: mouse CNS-1

<400> SEQUENCE: 17
cacaagggct gcaggaagag caatgcagcc cccacacact ggtccactgt gatgctcaga      60
gcggagatga cgaggtttgc tatatttaat tttggtgcct gcgtcacctc tgaccacaca     120
```

```
gcagcccaga cagagcaggg ctgggggagt ttcttaggcc ctctgcgagg ggatcacttt      180
ccactcgaga tggcactgtg gagggggagg aagagagagc aacagaaagt gaggtcgtaa      240
gtagaaaatt gcttctggga tttcgagtgg cttcgtcatg gggccctccc tggctgccga      300
gaaatcagtt gatctgggaa agttcgttgc aagccatgcg ctctgtcgct tttgggtgga      360
gccgagaaat gaatgaagat aatgaggcct cgtgactttt agttttcaca gtgagagggg      420
gcactgtggg ggaaggtggc tatggacaca gctctaggcc tga                       463

<210> SEQ ID NO 18
<211> LENGTH: 366
<212> TYPE: DNA
<213> ORGANISM: Mus musculus
<220> FEATURE:
<223> OTHER INFORMATION: mouse CNS-2

<400> SEQUENCE: 18
ctgtgtggga aagtgatcgt gaggagggct acttcaaaaa cagcctgttt cctctcagca       60
tttatcttgg gcttcctgcg acccaacctt caagtcactt ttatcagtgt tatcagaaca      120
tcacgtcgtc ttacccaaac accgttatgg ctctcgctga agcacaggac agatcagacg      180
ctctcccaca ctgcttccct cccccagccc cttgggaggg ctggggaaat tgagtttag       240 tcaaaggctg catctctctg attgtagcta agaactcaac tgggacttta cagccgaata      300
caattttctc agagtccgat atcaatctta acaaagagga tattgcctaa cccaacctaa      360
aagttg                                                                 366

<210> SEQ ID NO 19
<211> LENGTH: 150
<212> TYPE: DNA
<213> ORGANISM: Mus musculus
<220> FEATURE:
<223> OTHER INFORMATION: mouse CNS-3

<400> SEQUENCE: 19
ccttctaagg agccccaagt agttcagggc gtgatgccca ggtcctctgt gtgtagccag       60
ggctgtccaa ggccagagga aaccacagca ctctttcctt gatgggttgg tagagttggc      120
aggctccagt atgaacagac gcccttggga                                       150

<210> SEQ ID NO 20
<211> LENGTH: 201
<212> TYPE: DNA
<213> ORGANISM: Mus musculus
<220> FEATURE:
<223> OTHER INFORMATION: mouse CNS-4

<400> SEQUENCE: 20
gcactctggg actcacaagt tctgagaagt ggctgtgtcc aggactgaga caagttgatt       60
acaaatggct gtgacatcaa gctttggagc atgaagtatt gctggcccag tgaaggagaa      120
caagcattct cttccagaga agcatggtgt tccagtgcca gagagagatg gaccgcttcc      180
acagttcctc ataaggattg g                                                201

<210> SEQ ID NO 21
<211> LENGTH: 123
<212> TYPE: DNA
<213> ORGANISM: Mus musculus
<220> FEATURE:
<223> OTHER INFORMATION: mouse CNS-5
```

```
<400> SEQUENCE: 21 cccctttag caggcagagt ggtgactgaa gcattgggcc tgtggtttct gtaacaggaa    60
gtgatttaga tgccgaaagc taattttaga tgggttgata tggggttttc aaagaatgtt   120
tca                                                                123

<210> SEQ ID NO 22
<211> LENGTH: 118
<212> TYPE: DNA
<213> ORGANISM: Mus musculus
<220> FEATURE:
<223> OTHER INFORMATION: mouse CNS-6

<400> SEQUENCE: 22
gctagaaaac cactatcctg actcagtgac ttgccccacc ctggcctctg cccaaattc     60 tggaggcttt agtcaggaag taggggtctg tttgcccagg gctggggttt ccctgtag    118

<210> SEQ ID NO 23
<211> LENGTH: 164
<212> TYPE: DNA
<213> ORGANISM: Mus musculus
<220> FEATURE:
<223> OTHER INFORMATION: mouse CNS-7

<400> SEQUENCE: 23
tgggcaagtg ccaagatctt tagcctgaga gcttggggct gccccagctt ctaggctgga    60
ggaagtatga gagattgcca aagacctggg tttctctcca tcctgctgct tcctttgagg   120
tggttcccaa atccaccaag tggggaaaag acttagcttc tgtg                   164

<210> SEQ ID NO 24
<211> LENGTH: 181
<212> TYPE: DNA
<213> ORGANISM: Mus musculus
<220> FEATURE:
<223> OTHER INFORMATION: mouse CNS-8

<400> SEQUENCE: 24
cagagcgata gagcatttgg tttaactgag ctaaagtaaa cgctgcaaaa cctgaggaag    60
tgacttcagc atctgcaaat attccagaag gtctctgtgc caggaaaggt cagctgagga   120
ccagaagagc agggattcca aagtatactt aggagaaatg tgagccctg ggaagcgtta   180 c                                                                  181

<210> SEQ ID NO 25
<211> LENGTH: 175
<212> TYPE: DNA
<213> ORGANISM: Mus musculus
<220> FEATURE:
<223> OTHER INFORMATION: mouse CNS-9

<400> SEQUENCE: 25
ggcctctccg tgactcccag tgactgatat ttgcacctgg taactgaggt caggttactt    60
cttttaagtc acatgttttg ctttagggca ggaaggtgtt ggagccactt gttgcaaaga   120
cactgggagg tgatcacagc attgttgcaa acctcggctg gcagcagaga ttttg        175

<210> SEQ ID NO 26
<211> LENGTH: 239
<212> TYPE: DNA
<213> ORGANISM: Mus musculus
<220> FEATURE:
<223> OTHER INFORMATION: mouse CNS-10
```

-continued

```
<400> SEQUENCE: 26
agcttgctac aagatgactc agccagcaca agaggtgcat tcaggtccct gtaggtggag    60
gaagttcctg gaagcagagg tgtctgggat gtggccagct ccattgagct tggggagttc   120
tggtcaaaga gggctcgaag ccaggaaacc gtgactccca gccgcccctct ctaagcattg   180 tctcctgagt tctcaaggca agcccatttc ctagactagg caaccgaggt gcaaagaag    239

<210> SEQ ID NO 27
<211> LENGTH: 151
<212> TYPE: DNA
<213> ORGANISM: Mus musculus
<220> FEATURE:
<223> OTHER INFORMATION: mouse CNS-11

<400> SEQUENCE: 27
gactggaaaa ttttggcaaa ctgtcacaat gttctcgtgt cccgagaact caacatcact    60
gggcctcaga agctctcagg ggacagacaa taagaccaca gtctgtacag agccttctgt   120
gtggctctga cagctggggg agaaacaatc g                                 151

<210> SEQ ID NO 28
<211> LENGTH: 217
<212> TYPE: DNA
<213> ORGANISM: Mus musculus
<220> FEATURE:
<223> OTHER INFORMATION: mouse CNS-12

<400> SEQUENCE: 28
aggaaaaagc aagcactgtc cacattttct tacctttgat tttgtgttta tcaagggaaa    60
tcttgtttcc agttttatag catgtgttta tgacttgaa ccaggaactt gccctcctgg    120
cctcctgctt tatcctgttt cccgagttgc tccgtttgag gttgtgtaag acttgttaga   180
gggtttgctg ccacatcaaa gggcagggaa acctcct                            217

<210> SEQ ID NO 29
<211> LENGTH: 168
<212> TYPE: DNA
<213> ORGANISM: Mus musculus
<220> FEATURE:
<223> OTHER INFORMATION: mouse CNS-13

<400> SEQUENCE: 29
gcagctcagc cggtctttaa gccgtgtttg gttccatgga acacagaaga gggtgtggct    60
atagcaaagg gactttccca gttccagttt tgtgccattc aatccctcaa caacaactta   120
gcaaatgctg gctgtgtgtc tagcctagac agagtcaacg ggactcaa                168

<210> SEQ ID NO 30
<211> LENGTH: 210
<212> TYPE: DNA
<213> ORGANISM: Mus musculus
<220> FEATURE:
<223> OTHER INFORMATION: mouse CNS-14

<400> SEQUENCE: 30
ctatcatggt gttgaatcac tctgaaacct tggtggagtt actaaaattg caaattactt    60
ggcaattccc ctgaaacctt catctaagcc cacactttct cagagtagcc agaagatgtc   120
tgaagggaaa tagaattatt gtctcacgac ctctgggca agccaggtcc tgccagagct   180
aagcttggat tttgagagca tcattttaag                                    210
```

```
<210> SEQ ID NO 31
<211> LENGTH: 198
<212> TYPE: DNA
<213> ORGANISM: Mus musculus
<220> FEATURE:
<223> OTHER INFORMATION: mouse CNS-15

<400> SEQUENCE: 31
tggcagccgc ggcagccaat gggcagtgaa gactgttgct agggtcactg tgaaccttat    60
ttggtgacac ggggctgacc gtgcgttcac ctctgagaac cctgagaaac accaaccaca   120
gctcagcact atgaacgtct caaaaccaca gctgcatttc ctccaagaga agactcgact   180 ctccccttc ctgtctcc                                                  198

<210> SEQ ID NO 32
<211> LENGTH: 310
<212> TYPE: DNA
<213> ORGANISM: Mus musculus
<220> FEATURE:
<223> OTHER INFORMATION: mouse CNS-16

<400> SEQUENCE: 32
gagactgagg ccctgcagct ctggggactg cgtggagtga gggaattgag ggcttccttg    60
tctgctgaga aagcttccat ttttgactgc attctcccac atccttggga gggtttgagg   120
ctggaccgaa ggccttggct gacttagggc cacgttggcc gatagtgtgc agaggcctgg   180
ggggtgtgtc cctggcttct gggatctgtc aagagcttaa ttttatgcag atggaggttg   240
acagcaaatg ctgcaatgca ggcacgggaa agaccagcag agtcctggaa agaggcttca   300
actttgaaaa                                                          310

<210> SEQ ID NO 33
<211> LENGTH: 224
<212> TYPE: DNA
<213> ORGANISM: Homo sapiens
<220> FEATURE:
<223> OTHER INFORMATION: human CNS-1 core reverse complement

<400> SEQUENCE: 33
tgatttctcg gcagccaggg agggccccat gacaaagcca tttgaaatcc cagaagcaat    60
tttctactta cgacctcact ttctgttgct gtctctccct tcccctctgc tataccttt   120 cttggggaaa gtgattctct cacagcgtcg ttcagaaaca cccccagcca tgtgctgcct   180
gcctgggcag acgctgctgt gtggtcagag gtgacgcagg cacc                    224

<210> SEQ ID NO 34
<211> LENGTH: 214
<212> TYPE: DNA
<213> ORGANISM: Mus musculus
<220> FEATURE:
<223> OTHER INFORMATION: mouse CNS-1 core reverse complement

<400> SEQUENCE: 34
tgatttctcg gcagccaggg agggccccat gacgaagcca ctcgaaatcc cagaagcaat    60
tttctactta cgacctcact ttctgttgct ctctcttcct cccctccac agtgccatct   120 cgagtggaaa gtgatcccct cgcagagggc ctaagaaact cccccagccc tgctctgtct   180
gggctgctgt gtggtcagag gtgacgcagg cacc                               214
```

```
<210> SEQ ID NO 35
<211> LENGTH: 214
<212> TYPE: DNA
<213> ORGANISM: Rattus norvegicus
<220> FEATURE:
<223> OTHER INFORMATION: rat CNS-1 core reverse complement

<400> SEQUENCE: 35
tgatttctcg gcagccaggg agggccccat gacgaagcca ctcgaaatcc cagaagcaat      60
tttctactta cgacctcact ttctgttgtt ctctcttcct ccccctccat agtgccatct     120
tgagtggaaa gtgatcccct cacagaggac ctaagaaacg cccccagccc tgccctgtct     180
gggctgctgt gtggtcagag gtgacgcagg cacc                                 214

<210> SEQ ID NO 36
<211> LENGTH: 200
<212> TYPE: DNA
<213> ORGANISM: Oryctolagus cuniculus
<220> FEATURE:
<223> OTHER INFORMATION: rabbit CNS-1 core reverse complement

<400> SEQUENCE: 36
tgatttctcg gcagccaggg agggccccac gacaagccat tcaaaatccc agaagtgatt      60
ttctacttac gacctcactt tctgttgctc tctccttccc tccacatgcc ttctctgtgg     120
aaagtcaccc tctgaaacac ccccagcccg tgcactgcct gggcagatgc tactgtgtgg     180
tcagaggtga cgcaggcacc                                                 200

<210> SEQ ID NO 37
<211> LENGTH: 218
<212> TYPE: DNA
<213> ORGANISM: Canis familiaris
<220> FEATURE:
<223> OTHER INFORMATION: dog CNS-1 core reverse complement

<400> SEQUENCE: 37
tgatttctcg gcagccaggg agggccccat gacgaagcca tttgaaatcc cagaagcgat      60
tttctaccta cgacctcact ttctgttgcg ctcactccct tcccctgcac catgccttct     120
cttgtggaaa gtgagctctc agagcgtcct tcagaaacgc cccagcagat gcaccgccgg     180
gccgatgcta ctgtgtggtc agaggtgacg caggcacc                             218

<210> SEQ ID NO 38
<211> LENGTH: 220
<212> TYPE: DNA
<213> ORGANISM: Bos taurus
<220> FEATURE:
<223> OTHER INFORMATION: cow CNS-1 core reverse complement

<400> SEQUENCE: 38
tgatttctcg gcagccaggg agggccccat gacgaagcca tttgaaatcc cagaagcaat      60
tttctactta cgacctcact ttctgttgcg ttctctccct tccctcctg agtgtcttct     120 cttgtggaaa gtgattctct caaagcatcg ttcagaaacg cccccagccc gcgctgcctg     180
ggcagatggc tgctgtgtgg tcagaggtga cgcaggcacc                           220

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence:PCR primer
      CNS1 - forward
```

-continued

```
<400> SEQUENCE: 39
tgatttctcg gcagccaggg agggcc                                              26

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence:PCR primer
      CNS1 - reverse

<400> SEQUENCE: 40
ggtgcctgcg tcacctctga ccacac                                              26

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence:PCR primer
      CNS2 - forward

<400> SEQUENCE: 41
cctctcagca tttatcttgg gc                                                  22

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence:PCR primer
      CNS2 - reverse
<221> NAME/KEY: modified_base
<222> LOCATION: (11)..(12)
<223> OTHER INFORMATION: n = g, a, c or t

<400> SEQUENCE: 42
agagccataa nngtgtttgg g                                                   21

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence:PCR primer
      CNS3 - forward
<221> NAME/KEY: modified_base
<222> LOCATION: (1)..(27)
<223> OTHER INFORMATION: n = g, a, c or t

<400> SEQUENCE: 43
cnagtngntc agggcnngat gcccagg                                             27

<210> SEQ ID NO 44
<211> LENGTH: 29
<212> TYPE: DNA
<213> ORGANISM: Artificial Sequence
<220> FEATURE:
<223> OTHER INFORMATION: Description of Artificial Sequence:PCR primer
      CNS3 - reverse
<221> NAME/KEY: modified_base
<222> LOCATION: (1)..(29)
<223> OTHER INFORMATION: n = g, a, c or t

<400> SEQUENCE: 44
aagggngtct gntcntnctg gagcctgcc                                           29
```

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence:PCR primer
      CNS4 - forward
<221> NAME/KEY: modified_base
<222> LOCATION: (1)..(20)
<223> OTHER INFORMATION: n = g, a, c or t

<400> SEQUENCE: 45
gcatgaagna ttgntggccc                                                   20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence:PCR primer
      CNS4 - reverse
<221> NAME/KEY: modified_base
<222> LOCATION: (10)
<223> OTHER INFORMATION: n = g, a, c or t

<400> SEQUENCE: 46
ctctctggcn ctggaacacc                                                   20

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence:PCR primer
      CNS5 - forward
<221> NAME/KEY: modified_base
<222> LOCATION: (1)..(22)
<223> OTHER INFORMATION: n = g, a, c or t

<400> SEQUENCE: 47
acngtttttn gtgtgcagca ct                                                22

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence:PCR primer
      CNS5 - reverse
<221> NAME/KEY: modified_base
<222> LOCATION: (8)
<223> OTHER INFORMATION: n = g, a, c or t

<400> SEQUENCE: 48
attctttnaa aaccccatat c                                                 21

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence:PCR primer
      CNS6 - forward
<221> NAME/KEY: modified_base
<222> LOCATION: (1)..(20)
<223> OTHER INFORMATION: n = g, a, c or t

<400> SEQUENCE: 49
tagnanagtg aggatgtctg                                                   20

```
<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence:PCR primer
      CNS6 - reverse
<221> NAME/KEY: modified_base
<222> LOCATION: (11)
<223> OTHER INFORMATION: n = g, a, c or t

<400> SEQUENCE: 50 aaacccagc nctgggcaaa cag                                              23

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence:PCR primer
      CNS8 - forward
<221> NAME/KEY: modified_base
<222> LOCATION: (1)..(21)
<223> OTHER INFORMATION: n = g, a, c or t

<400> SEQUENCE: 51
aagtaaacnc tgnaaaannt g                                               21

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence:PCR primer
      CNS8 - reverse
<221> NAME/KEY: modified_base
<222> LOCATION: (1)..(23)
<223> OTHER INFORMATION: n = g, a, c or t

<400> SEQUENCE: 52
cncnnaagta tactttggaa tcc                                             23

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence:PCR primer
      CNS9 - forward
<221> NAME/KEY: modified_base
<222> LOCATION: (1)..(23)
<223> OTHER INFORMATION: n = g, a, c or t

<400> SEQUENCE: 53
tnactcncag tgactgatnt ttg                                             23

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence:PCR primer
      CNS9 - reverse
<221> NAME/KEY: modified_base
<222> LOCATION: (1)..(24)
<223> OTHER INFORMATION: n = g, a, c or t

<400> SEQUENCE: 54
atcncctccn ngtntctttg caac                                            24
```

```
<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence:PCR primer
      CNS10 - forward
<221> NAME/KEY: modified_base
<222> LOCATION: (3)
<223> OTHER INFORMATION: n = g, a, c or t

<400> SEQUENCE: 55
cangatgact cagccagcac aag                                        23

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence:PCR primer
      CNS10 - reverse
<221> NAME/KEY: modified_base
<222> LOCATION: (4)..(5)
<223> OTHER INFORMATION: n = g, a, c or t

<400> SEQUENCE: 56
cctnntctag gaaatgggct tgc                                        23

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence:PCR primer
      CNS11 - forward
<221> NAME/KEY: modified_base
<222> LOCATION: (7)
<223> OTHER INFORMATION: n = g, a, c or t

<400> SEQUENCE: 57
ggcaaantgt cacaatgttc                                            20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence:PCR primer
      CNS11 - reverse
<221> NAME/KEY: modified_base
<222> LOCATION: (7)
<223> OTHER INFORMATION: n = g, a, c or t

<400> SEQUENCE: 58
ctgtcanagc cacacagaag                                            20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence:PCR primer
      CNS12 - forward
<221> NAME/KEY: modified_base
<222> LOCATION: (14)
<223> OTHER INFORMATION: n = g, a, c or t

<400> SEQUENCE: 59
tccacatttt cttncctttg                                            20
```

```
<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence:PCR primer
      CNS12 - reverse
<221> NAME/KEY: modified_base
<222> LOCATION: (1)..(19)
<223> OTHER INFORMATION: n = g, a, c or t

<400> SEQUENCE: 60
gtntcnctgc cctttgatg                                                    19

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence:PCR primer
      CNS13 - forward
<221> NAME/KEY: modified_base
<222> LOCATION: (1)..(20)
<223> OTHER INFORMATION: n = g, a, c or t

<400> SEQUENCE: 61
ggntgagatn ctggaggctc                                                   20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence:PCR primer
      CNS13 - reverse
<221> NAME/KEY: modified_base
<222> LOCATION: (14)..(15)
<223> OTHER INFORMATION: n = g, a, c or t

<400> SEQUENCE: 62
gagcaggtct gacnngggtg                                                   20

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence:PCR primer
      CNS14 - forward

<400> SEQUENCE: 63
ttggcaattc ccctgaaa                                                     18

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence:PCR primer
      CNS14 - reverse

<400> SEQUENCE: 64
aagctkagyt ctggcagg                                                     18

<210> SEQ ID NO 65
<211> LENGTH: 24
<212> TYPE: DNA
<213> ORGANISM: Artificial Sequence
```

-continued

```
<220> FEATURE:
<223> OTHER INFORMATION: Description of Artificial Sequence:PCR primer
      CNS15 - forward
<221> NAME/KEY: modified_base
<222> LOCATION: (1)..(24)
<223> OTHER INFORMATION: n = g, a, c or t

<400> SEQUENCE: 65
aagnntgttg ctanggtcac tgtg                                            24

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence:PCR primer
      CNS15 - reverse
<221> NAME/KEY: modified_base
<222> LOCATION: (1)..(24)
<223> OTHER INFORMATION: n = g, a, c or t

<400> SEQUENCE: 66
gcagntgtgg ttttgagang ttca                                            24

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence:PCR primer
      CNS16 - forward

<400> SEQUENCE: 67
ctcccacatc cttgggaggg                                                 20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence:PCR primer
      CNS16 - reverse
<221> NAME/KEY: modified_base
<222> LOCATION: (5)
<223> OTHER INFORMATION: n = g, a, c or t

<400> SEQUENCE: 68
ccagnagcca gggacacacc                                                 20

<210> SEQ ID NO 69
<211> LENGTH: 39
<212> TYPE: DNA
<213> ORGANISM: Artificial Sequence
<220> FEATURE:
<223> OTHER INFORMATION: Description of Artificial Sequence:
      oligonucleotide LoxP-Pml I forward

<400> SEQUENCE: 69
gtgtaacttc gtatagcata cattatacga agttatcac                            39

<210> SEQ ID NO 70
<211> LENGTH: 39
<212> TYPE: DNA
<213> ORGANISM: Artificial Sequence
<220> FEATURE:
<223> OTHER INFORMATION: Description of Artificial Sequence:
      oligonucleotide LoxP-Pml I reverse
```

-continued

```
<400> SEQUENCE: 70
gtgataactt cgtataatgt atgctatacg aagttacac                              39

<210> SEQ ID NO 71
<211> LENGTH: 39
<212> TYPE: DNA
<213> ORGANISM: Artificial Sequence
<220> FEATURE:
<223> OTHER INFORMATION: Description of Artificial Sequence:
      oligonucleotide LoxP-SphI forward

<400> SEQUENCE: 71
ctaacttcgt atagcataca ttatacgaag ttatgcatg                              39

<210> SEQ ID NO 72
<211> LENGTH: 39
<212> TYPE: DNA
<213> ORGANISM: Artificial Sequence
<220> FEATURE:
<223> OTHER INFORMATION: Description of Artificial Sequence:
      oligonucleotide LoxP-SphI reverse

<400> SEQUENCE: 72
cataacttcg tataatgtat gctatacgaa gttagcatg                              39

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence:human probe
      1 forward

<400> SEQUENCE: 73
caggtggcat cttggaaact gtcc                                              24

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence:human probe
      1 reverse

<400> SEQUENCE: 74
agacctacct tgccaagggc ttcc                                              24

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence:human probe
      2 forward

<400> SEQUENCE: 75
caggtggcat cttggaaact gtcc                                              24

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence:human probe
      2 reverse
```

```
<400> SEQUENCE: 76
agacctacct tgccaagggc ttcc                                        24

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence:mouse probe
      3 forward

<400> SEQUENCE: 77
gagtaaggca actccgctca g                                           21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence:mouse probe
      3 reverse

<400> SEQUENCE: 78
ctggctgaca ctcttcatcc c                                           21

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence:TaqMan
      primer hIL-4 - forward

<400> SEQUENCE: 79
acagcctcac agagcagaag act                                         23

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence:TaqMan
      primer hIL-4 - reverse

<400> SEQUENCE: 80
gtgttcttgg aggcagcaaa g                                           21

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence:TaqMan
      primer hIL-5 - forward

<400> SEQUENCE: 81
ataaaaatca ccaactgtgc actgaa                                      26

<210> SEQ ID NO 82
<211> LENGTH: 29
<212> TYPE: DNA
<213> ORGANISM: Artificial Sequence
<220> FEATURE:
<223> OTHER INFORMATION: Description of Artificial Sequence:TaqMan
      primer hIL-5 - reverse
```

```
<400> SEQUENCE: 82 caagttttg aatagtcttt ccacagtac                                      29

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence:TaqMan
      primer hIL-13 - forward

<400> SEQUENCE: 83
cagaagctcc gctctgcaat                                               20

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence:TaqMan
      primer hIL-13 - reverse

<400> SEQUENCE: 84
acacgttgat cagggattcc a                                             21

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence:TaqMan
      primer hKIF3A - forward

<400> SEQUENCE: 85
cgcagtctcg agagcgtcaa                                               20

<210> SEQ ID NO 86
<211> LENGTH: 16
<212> TYPE: DNA
<213> ORGANISM: Artificial Sequence
<220> FEATURE:
<223> OTHER INFORMATION: Description of Artificial Sequence:TaqMan
      primer hKIF3A - reverse

<400> SEQUENCE: 86
acaccgggtg cgcaga                                                   16

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence:TaqMan
      primer hRAD50 - forward

<400> SEQUENCE: 87
tgttggctgg caggatcttt                                               20

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence:TaqMan
      primer hRAD50 - reverse
```

-continued

```
<400> SEQUENCE: 88
cgtgagaccc gcgaatct                                                  18

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence:TaqMan
      primer mGAPDH - forward

<400> SEQUENCE: 89
ggcaaattca acggcacagt                                                20

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence:TaqMan
      primer mGAPDH - reverse

<400> SEQUENCE: 90
cctcacccca tttgatgtta gtg                                            23
```

COORDINATE CYTOKINE REGULATORY SEQUENCES

CROSS-REFERENCES TO RELATED APPLICATIONS

This application claims priority to provisional application U.S. Ser. No. 60/183,657, filed Feb. 18, 2000, the disclosure of which is herein incorporated by reference in its entirety.

STATEMENT AS TO RIGHTS TO INVENTIONS MADE UNDER FEDERALLY SPONSORED RESEARCH AND DEVELOPMENT

The present invention was made under funding from the United States Department of Energy under Contract DE-AC03-76SF0098 for the management and operation of the Lawrence Berkeley National Laboratory. The present invention was also made under funding from NIH GM-5748202 (K.A.F.), HHMI AI30663 and NIH HL56385 (R.M.L.). The United States Government has certain rights to this invention.

FIELD OF THE INVENTION

The present invention involves modulation of the expression of cytokine genes, in particular interleukin-4 (IL-4), interleukin-13 (IL-13), and interleukin-5 (IL-5), by means of non-coding genomic regions newly identified as affecting levels of expression of these genes. The expression of these cytokines is mediated by certain conserved non-coding sequences (CNS) located in the genomic region containing the genes for these cytokines. These sequences are identified herein as CNS sequences 1 through 16, also referred to as CR 1 through 16 in provisional application 60/183,657.

BACKGROUND OF THE INVENTION

The recent scale-up of efforts to complete the sequence of the human genome is producing ever-increasing amounts of unannotated DNA sequence. Computational methods for recognizing coding sequences in genomic DNA, gene prediction programs coupled with similarity searches in protein and cDNA databases, are well established and capable of detecting the majority of genes. However, identifying regulatory elements in the 95% of the genome comprised of non-coding sequences is currently a significantly greater and largely unmet challenge. Numerous experimental studies have demonstrated that regulatory elements tend to be evolutionarily conserved among vertebrates (Li et al., *Trends Genet.* 15:403 (1999)). Thus, cross-species genomic sequence comparisons provide a potential means for identifying these non-coding sequences of biologic import (Hardison et al., *Genome Res.* 7:959 (1997)).

Extensive studies have focused on understanding the regulation of the five biomedically important cytokine genes clustered at human 5q31. As evidenced by significant sequence differences between orthologous cytokine genes in different mammals (on average ~50% identity between humans and mice), these genes are rapidly evolving. However, several of the cytokines in this interval, interleukin-4 (IL-4), interleukin-13 (IL-13), and interleukin-5 (IL-5) have physically remained in close proximity to each other in all species studied to date. This observation, coupled with the fact that IL-4, IL-13, and IL-5 are coordinately co-activated in T helper 2-type ($T_H2$) cells (Abbas et al., *Nature* 383:787 (1996)), suggests that the clustering of these genes may be due to commonly shared, as of yet unidentified, cis-regulatory sequences. Studies examining human 5q31 YAC transgenic mice demonstrated that the human IL-4, IL-13 and IL-5 transgenes are appropriately regulated in a site-of-integration-independent manner in murine $T_H2$ cells (Symula et al., *Nature Genet.* 23:241 (1999)), suggesting that the regulatory elements controlling the expression of these cytokines are conserved in humans and mice. However, regulatory elements, such as locus control regions (LCRs), have been difficult to identify.

Enhanced expression of cytokines has been associated with inflammation, autoimmune disorders, and numerous allergic diseases. It would be desirable to identify regulatory elements that control the production of cytokine genes. By understanding and controlling the production of cytokines, such as IL-4, IL-5, and IL-13, disease states can be improved and treated. Embodiments of the invention meet this and other goals.

SUMMARY OF THE INVENTION

The LCR elements in the interleukin gene cluster region of the chromosome, referred to as CNS sequences, have been identified using comparative analysis between different mammals. The term "locus control region" refers to a long-range cis-acting regulatory element that confers high level of expression of linked genes, such as the β-globin gene expression locus control region or the cytokine gene expression locus control region. LCRs are physically comprised of varying numbers of large ($\geq 100$ bp in length) highly conserved ($\geq 70\%$ identity among mammals) non-coding sequences. The comparison of similarities between genetic information among mammals is enabled through the use of computational programs that compare the percentage of similarity between the different groups of mammals.

Sixteen LCR elements are identified and characterized, which elements are interspersed throughout the human 5q31 interleukin and mouse chromosome 11 interleukin gene cluster regions. These sixteen LCR elements are referred to as CNS-1 through CNS-16 sequences. The locations of CNS sequences and various genes within the human 5q31 chromosomal region are shown in FIG. 1. In the mouse chromosome 11, the sixteen CNS sequences and various cytokine genes are found in the same order as in the human 5q31 chromosomal region.

The CNS sequences modulate expression of one or more cytokine genes. For example, the CNS-1 sequence, which is located in the intergenic region between IL-4 and IL-13, is found to modulate IL-4, IL-13 and IL-5 in a specific manner. This finding is based on studies on T cells derived from transgenic animals. Specifically, multiple lines of mice were created bearing a 450-kb human yeast artificial chromosome (YAC) comprising a portion of the human 5q31 chromosomal region. One line of mice lacked the human CNS-1 sequence. Another line possessed the human CNS-1 sequence. Experimental results indicate that the presence of the human CNS-1 sequence increases the likelihood that human 5q31 $T_H2$ cytokines will be expressed. However, the CNS sequence does not act as a classical silencer or enhancer and may actually alter chromatin structure. In another example, the CNS-2 sequence, located between IL-4 and KIF3A, acts as an enhancer for the IL-4 gene expression.

These and other findings described herein have strong implications in the medical and pharmaceutical fields because of the potential benefits in controlling prevalent illnesses and conditions. For example, enhanced expression of these cytokines has been associated with inflammation, autoimmune disorders, and numerous allergic diseases. By controlling the production of cytokines, such as IL-4, IL-5, and IL-13, by modulating the CNS sequences, disease states can be improved and treated. Moreover, the CNS sequences of the present invention can be used as a diagnostic tool to screen patients having diseases related to cytokine gene expression.

As such, in one aspect the invention provides an isolated nucleic acid molecule having a length of about 1000 nucleotides of less, wherein the nucleic acid molecule has a sequence at least about 70% identical, or about 90% identical to SEQ ID NO:1 or a complement thereof, wherein SEQ ID NO:1 is a CNS-1 sequence from human. In one embodiment, an isolated molecule has a sequence of SEQ ID NO:1 or SEQ ID NO:17 (a CNS-1 sequence from mouse) or a subsequent thereof.

In another aspect, the invention provides an expression cassette comprising a CNS-1 sequence operably linked to a promoter which controls the transcription of a heterologous coding sequence, wherein the CNS-1 sequence has a sequence at least about 70% identical to SEQ ID NO:1, preferably has a sequence or subsequence of SEQ ID NO:1 or SEQ ID NO:17. In these embodiments, the promoter that controls the transcription of a heterologous coding sequence, such as a reporter gene, is located within 5 kilobases, 3 kilobases, or 1 kilobases, preferably within 100 nucleotides, from the promoter. Preferably, the promoters that drive the expression of the reporter gene in the expression cassette is a human IL-4 gene promoter or a human IL-13 gene promoter.

In another aspect, the invention provides expression cassette comprising or consisting essentially of an IL-4 gene, an IL-13 gene and a CNS-1 sequence. In a preferred embodiment, the expression cassette comprises a portion of the human 5q31 chromosomal region, and wherein the IL-4 gene, the IL-13 gene and the CNS-1 sequence are located within the portion of the human 5q31 chromosomal region in their native organization.

In another aspect, the invention provides an expression cassette comprising an IL-4 gene, an IL-13 gene, and a CNS-1 sequence flanked between two recombination site sequences. This construct is particularly useful in making two lines of non-human transgenic animals that are identical, except one line has the CNS-1 sequence and the other line lacks the CNS-1 sequence.

In another aspect, the invention provides an expression cassette comprising an IL-4 gene and an IL-13 gene and lacking a CNS-1 sequence. In one embodiment, the expression cassette comprises a portion of the human 5q31 chromosomal region which has a deletion of CNS-1, and wherein the IL4-gene and the IL-13 gene are located within the portion of the human 5q31 chromosomal region in their native organization. In another embodiment, the expression cassette comprises a marker gene between the IL-4 gene and the IL-13 at the site where CNS-1 is deleted.

In another aspect, the invention provides T cells that comprise an expression cassette described herein. Preferably, the T cells are derived from human or mouse. In one embodiment, the T cells are stimulated to differentiate into $T_H1$ or $T_H2$ phenotype. In another embodiment, the T cells have a deletion of one or more of its native CNS sequences within the cells' chromosome.

In another aspect, the invention provides non-human transgenic animals comprising an expression cassette described herein. In one embodiment, in a transgenic animal, its native CNS-1 sequence is deleted from the chromosome. For example, a mouse lacking CNS-1 sequence from the endogenous chromosome 11 (i.e., knockout mouse) is provided. In another embodiment, transgenic animals comprising a transgene (e.g., a human CNS-1 sequence) are provided.

In another aspect, the invention provides methods for identifying a compound that modulates binding of a transcription factor to a CNS-1 sequence, the method comprising: (a) contacting the compound with the T cells described herein; and (b) determining the functional effect of the compound on binding of the transcription factor to the CNS-1 sequence. In one embodiment, the compound being tested is an antisense sequence of the CNS sequence. In another embodiment, the compound being tested is an antibody against the transcription factor that binds to a CNS sequence.

Definitions

The term "locus control region" refers to a long-range cis-acting regulatory element that confers high level of expression of linked genes, such as the β-globin gene expression locus control region or the cytokine gene expression locus control region. LCRs are physically comprised of varying numbers of large (≧100 bp in length) highly conserved (≧70% identity among mammals) non-coding sequences.

The term "cytokine" refers to soluble glycoproteins released by cells of the immune system, which act nonenzymatically through specific receptors to regulate immune responses. Common cytokines in allergology include, interleukins, lymphokines, interferons, colony stimulator factors, platelet-activating factors, and tumor necrosis factors. Cytokines that are found in the human 5q31 chromosomal region (and in the mouse chromosome 11) include interleukin-4 ("IL-4"), interleukin-13 ("IL-13"), interleukin-5 ("IL-5"), granulocyte-macrophage-colony stimulating factor ("GMCSF"), interleukin-3 ("IL-3"), and IRF-1.

The term "CNS sequence" refers to a long-range cis acting regulatory element found in the cytokine gene cluster region of the chromosome.

The CNS sequences can comprise varying numbers of large highly conserved (≧70% identity among mammals) non-coding sequences. Ninety human/mouse conserved regions were identified in the cytokine gene cluster regions of the human and mouse chromosome. Among these, sixteen CNS sequences were analyzed in depth and are referred to as CNS-1 through CNS-16. In human, these sixteen CNS sequences are located at the 5q31 chromosomal region. In mouse, the corresponding sixteen CNS sequences are located at chromosome 11 in the same order as found in the human 5q31 chromosomal region.

The term "CNS-1 sequence" refers to a long-range cis acting regulatory element located in the intergenic region between the IL-4 gene and the IL-13 gene. The presence of CNS-1 sequence increases the IL-4, IL-13 and IL-5 gene expression. The CNS-1 sequence is highly conserved (e.g., greater than 70% identity) among mammals. For example, in human a CNS-1 sequence has a sequence of SEQ ID NO:1 and in mouse a CNS-1 sequence has a sequence of SEQ ID NO:17, wherein the two sequences share about 84% sequence identity. Accordingly, the term "CNS-1 sequence" refers to polymorphic variants, alleles, interspecies homologs, and mutants that: (1) have about 70% nucleotide sequence identity, preferably about 80% nucleotide sequence identity, more preferably about 90% nucleotide sequence identity, even more preferably about 95% nucleotide sequence identity or higher to SEQ ID NO:1 or to SEQ ID NO:17, over a window of about at least 50–100 nucleotides; (2) specifically hybridize (with a size of at least about 50 nucleotides, preferably at least about 100 nucleotides) under stringent hybridization conditions to a sequence selected from a group consisting of SEQ ID NO:1 and SEQ ID NO:17; or (3) are amplified by primers that specifically hybridize under stringent hybridization conditions to SEQ ID NO:1 or SEQ ID NO:17. The term "CNS-1 sequence" can refer to any sequence that have properties described above and can be of any length as long as it comprises binding sites for transcription factor(s). For example, CNS-1 sequence can refer to a nucleotide sequence having 1000 nucleotides or less, 500 nucleotides or less, 400 nucleotides or less, 300 nucleotides or less, 200 nucleotides or less, 100 nucleotides or less, 50 nucleotides or less, 30 nucleotides or less, or 20 nucleotides or less.

The term "CNS-2 sequence" refers to a long-range cis acting regulatory element located downstream of the IL-4 gene. The presence of CNS-2 sequence increases the IL-4 gene expression. The CNS-2 sequence is highly conserved (e.g., greater than 70% identity) among mammals. For example, in human a CNS-2 sequence has a sequence of SEQ ID NO:2 and in mouse a CNS-2 sequence has a sequence of SEQ ID NO:18, wherein the two sequences share about 83% sequence identity. Accordingly, the term "CNS-2 sequence" refers to polymorphic variants, alleles, interspecies homologs, and mutants that: (1) have about 70% nucleotide sequence identity, preferably about 80% nucleotide sequence identity, more preferably about 90% nucleotide sequence identity, even more preferably about 95% nucleotide sequence identity or higher to SEQ ID NO:2 or to SEQ ID NO:18, over a window of about at least 50–100 nucleotides; (2) specifically hybridize (with a size of at least about 50 nucleotides, preferably at least about 100 nucleotides) under stringent hybridization conditions to a sequence selected from a group consisting of SEQ ID NO:2 and SEQ ID NO:18; or (3) are amplified by primers that specifically hybridize under stringent hybridization conditions to SEQ ID NO:2 or SEQ ID NO:18. The term "CNS-2 sequence" can refer to any sequence that have properties described above and can be of any length as long as it comprises binding sites for transcription factor(s). For example, CNS-2 sequence can refer to a nucleotide sequence having 1000 nucleotides or less, 500 nucleotides or less, 400 nucleotides or less, 300 nucleotides or less, 200 nucleotides or less, 100 nucleotides or less, 50 nucleotides or less, 30 nucleotides or less, or 20 nucleotides or less.

The term "CNS-3 sequence" refers to a long-range cis acting regulatory element located about 2–3 kilobases upstream of the RIL gene (previously called the LIM domain-pseudogene). The CNS-3 sequence is highly conserved (e.g., greater than 70% identity) among mammals. For example, in human a CNS-3 sequence has a sequence of SEQ ID NO:3 and in mouse a CNS-3 sequence has a sequence of SEQ ID NO:19, wherein the two sequences share about 76%. Accordingly, the term "CNS-3 sequence" refers to polymorphic variants, alleles, interspecies homologs, and mutants that: (1) have about 70% nucleotide sequence identity, preferably about 80% nucleotide sequence identity, more preferably about 90% nucleotide sequence identity, even more preferably about 95% nucleotide sequence identity or higher to SEQ ID NO:3 or to SEQ ID NO:19, over a window of about at least 50–100 nucleotides; (2) specifically hybridize (with a size of at least about 50 nucleotides, preferably at least about 100 nucleotides) under stringent hybridization conditions to a sequence selected from a group consisting of SEQ ID NO:3 and SEQ ID NO:19; or (3) are amplified by primers that specifically hybridize under stringent hybridization conditions to SEQ ID NO:3 or SEQ ID NO:19. The term "CNS-3 sequence" can refer to any sequence that have properties described above and can be of any length as long as it comprises binding sites for transcription factor(s). For example, CNS-3 sequence can refer to a nucleotide sequence having 1000 nucleotides or less, 500 nucleotides or less, 400 nucleotides or less, 300 nucleotides or less, 200 nucleotides or less, 100 nucleotides or less, 50 nucleotides or less, 30 nucleotides or less, or 20 nucleotides or less.

The term "CNS-4 sequence" refers to a long-range cis acting regulatory element located in the intergenic region between the RIL gene and the P4-hydroxylase alpha (II) gene. The CNS-4 sequence is highly conserved (e.g., greater than 70% identity) among mammals. For example, in human a CNS-4 sequence has a sequence of SEQ ID NO:4 and in mouse a CNS-4 sequence has a sequence of SEQ ID NO:20, wherein the two sequences share about 74% sequence identity. Accordingly, the term "CNS-4 sequence" refers to polymorphic variants, alleles, interspecies homologs, and mutants that: (1) have about 70% nucleotide sequence identity, preferably about 80% nucleotide sequence identity, more preferably about 90% nucleotide sequence identity, even more preferably about 95% nucleotide sequence identity or higher to SEQ ID NO:4 or to SEQ ID NO:20, over a window of about at least 50–100 nucleotides; (2) specifically hybridize (with a size of at least about 50 nucleotides, preferably at least about 100 nucleotides) under stringent hybridization conditions to a sequence selected from a group consisting of SEQ ID NO:4 and SEQ ID NO:20; or (3) are amplified by primers that specifically hybridize under stringent hybridization conditions to SEQ ID NO:4 or SEQ ID NO:20. The term "CNS-4 sequence" can refer to any sequence that have properties described above and can be of any length as long as it comprises binding sites for transcription factor(s). For example, CNS-4 sequence can refer to a nucleotide sequence having 1000 nucleotides or less, 500 nucleotides or less, 400 nucleotides or less, 300 nucleotides or less, 200 nucleotides or less, 100 nucleotides or less, 50 nucleotides or less, 30 nucleotides or less, or 20 nucleotides or less.

The term "CNS-5 sequence" refers to a long-range cis acting regulatory element located in the intergenic region between the P4-hydroxylase alpha(II)-pseudogene and the GMCSF gene. The CNS-5 sequence is highly conserved (e.g., greater than 70% identity) among mammals. For example, in human a CNS-5 sequence has a sequence of SEQ ID NO:5 and in mouse a CNS-5 sequence has a sequence of SEQ ID NO:21, wherein the two sequences share about 89% sequence identity. Accordingly, the term "CNS-5 sequence" refers to polymorphic variants, alleles, interspecies homologs, and mutants that: (1) have about 70% nucleotide sequence identity, preferably about 80% nucleotide sequence identity, more preferably about 90% nucleotide sequence identity, even more preferably about 95% nucleotide sequence identity or higher to SEQ ID NO:5 or to SEQ ID NO:21, over a window of about at least 50–100 nucleotides; (2) specifically hybridize (with a size of at least about 50 nucleotides, preferably at least about 100 nucleotides) under stringent hybridization conditions to a sequence selected from a group consisting of SEQ ID NO:5 and SEQ ID NO:21; or (3) are amplified by primers that specifically hybridize under stringent hybridization conditions to SEQ ID NO:5 or SEQ ID NO:21. The term "CNS-5 sequence" can refer to any sequence that have properties described above and can be of any length as long as it comprises binding sites for transcription factor(s). For example, CNS-5 sequence can refer to a nucleotide sequence having 1000 nucleotides or less, 500 nucleotides or less, 400 nucleotides or less, 300 nucleotides or less, 200 nucleotides or less, 100 nucleotides or less, 50 nucleotides or less, 30 nucleotides or less, or 20 nucleotides or less.

The term "CNS-6 sequence" refers to long-range cis acting regulatory element located in the intergenic region between the GMCSF and the IL-3 gene. The CNS-6 sequence is highly conserved (e.g., greater than 70% identity) among mammals. For example, in human a CNS-6 sequence has a sequence of SEQ ID NO:6 and in mouse a CNS-6 sequence has a sequence of SEQ ID NO:22, wherein the two sequences share about 91% sequence identity. Accordingly, the term "CNS-6 sequence" refers to polymorphic variants, alleles, interspecies homologs, and mutants that: (1) have about 70% nucleotide sequence identity, preferably about 80% nucleotide sequence identity, more preferably about 90% nucleotide sequence identity, even more preferably about 95% nucleotide sequence identity or higher to SEQ ID NO:6 or to SEQ ID NO:22, over a window of about at least 50–100 nucleotides; (2) specifically hybridize (with a size of at least about 50 nucleotides, preferably at least about 100 nucleotides) under stringent hybridization conditions to a sequence selected from a group consisting of SEQ ID NO:6 and SEQ ID NO:22; or (3) are amplified by primers that specifically hybridize under stringent hybridization conditions to SEQ ID NO:6 or SEQ ID NO:22. The term "CNS-6 sequence" can refer to any sequence that have properties described above and can be of any length as long as it comprises binding sites for transcription factor(s). For example, CNS-6 sequence can refer to a nucleotide sequence having 1000 nucleotides or less, 500 nucleotides or less, 400 nucleotides or less, 300 nucleotides or less, 200 nucleotides or less, 100 nucleotides or less, 50 nucleotides or less, 30 nucleotides or less, or 20 nucleotides or less.

The term "CNS-7 sequence" refers to a long-range cis acting regulatory element located in the intergenic region between the GMCSF and the IL-3 gene. The CNS-7 sequence is highly conserved (e.g., greater than 70% identity) among mammals. For example, in human a CNS-7 sequence has a sequence of SEQ ID NO:7 and in mouse a CNS-7 sequence has a sequence of SEQ ID NO:23, wherein the two sequences share about 76% sequence identity. Accordingly, the term "CNS-7 sequence" refers to polymorphic variants, alleles, interspecies homologs, and mutants that: (1) have about 70% nucleotide sequence identity, preferably about 80% nucleotide sequence identity, more preferably about 90% nucleotide sequence identity, even more preferably about 95% nucleotide sequence identity or higher to SEQ ID NO:7 or to SEQ ID NO:23, over a window of about at least 50–100 nucleotides; (2) specifically hybridize (with a size of at least about 50 nucleotides, preferably at least about 100 nucleotides) under stringent hybridization conditions to a sequence selected from a group consisting of SEQ ID NO:7 and SEQ ID NO:23; or (3) are amplified by primers that specifically hybridize under stringent hybridization conditions to SEQ ID NO:7 or SEQ ID NO:23. The term "CNS-7 sequence" can refer to any sequence that have properties described above and can be of any length as long as it comprises binding sites for transcription factor(s). For example, CNS-7 sequence can refer to a nucleotide sequence having 1000 nucleotides or less, 500 nucleotides or less, 400 nucleotides or less, 300 nucleotides or less, 200 nucleotides or less, 100 nucleotides or less, 50 nucleotides or less, 30 nucleotides or less, or 20 nucleotides or less.

The term "CNS-8 sequence" refers to a long-range cis acting regulatory element located in Hs.70932 region. The CNS-8 sequence is highly conserved (e.g., greater than 70% identity) among mammals. For example, in human a CNS-8 sequence has a sequence of SEQ ID NO:8 and in mouse a CNS-8 sequence has a sequence of SEQ ID NO:24, wherein the two sequences share about 77% sequence identity. Accordingly, the term "CNS-8 sequence" refers to polymorphic variants, alleles, interspecies homologs, and mutants that: (1) have about 70% nucleotide sequence identity, preferably about 80% nucleotide sequence identity, more preferably about 90% nucleotide sequence identity, even more preferably about 95% nucleotide sequence identity or higher to SEQ ID NO:8 or to SEQ ID NO:24, over a window of about at least 50–100 nucleotides; (2) specifically hybridize (with a size of at least about 50 nucleotides, preferably at least about 100 nucleotides) under stringent hybridization conditions to a sequence selected from a group consisting of SEQ ID NO:8 and SEQ ID NO:24; or (3) are amplified by primers that specifically hybridize under stringent hybridization conditions to SEQ ID NO:8 or SEQ ID NO:24. The term "CNS-8 sequence" can refer to any sequence that have properties described above and can be of any length as long as it comprises binding sites for transcription factor(s). For example, CNS-8 sequence can refer to a nucleotide sequence having 1000 nucleotides or less, 500 nucleotides or less, 400 nucleotides or less, 300 nucleotides or less, 200 nucleotides or less, 100 nucleotides or less, 50 nucleotides or less, 30 nucleotides or less, or 20 nucleotides or less.

The term "CNS-9 sequence" refers to a long-range cis acting regulatory element located in Hs.70932 region. The CNS-9 sequence is highly conserved (e.g., greater than 70% identity) among mammals. For example, in human a CNS-9 sequence has a sequence of SEQ ID NO:9 and in mouse a CNS-9 sequence has a sequence of SEQ ID NO:25, wherein the two sequences share about 77% sequence identity. Accordingly, the term "CNS-9 sequence" refers to polymorphic variants, alleles, interspecies homologs, and mutants that: (1) have about 70% nucleotide sequence identity, preferably about 80% nucleotide sequence identity, more preferably about 90% nucleotide sequence identity, even more preferably about 95% nucleotide sequence identity or higher to SEQ ID NO:9 or to SEQ ID NO:25, over a window of about at least 50–100 nucleotides; (2) specifically hybridize (with a size of at least about 50 nucleotides, preferably at least about 100 nucleotides) under stringent hybridization conditions to a sequence selected from a group consisting of SEQ ID NO:9 and SEQ ID NO:25; or (3) are amplified by primers that specifically hybridize under stringent hybridization conditions to SEQ ID NO:9 or SEQ ID NO:25. The term "CNS-9 sequence" can refer to any sequence that have properties described above and can be of any length as long as it comprises binding sites for transcription factor(s). For example, CNS-9 sequence can refer to a nucleotide sequence having 1000 nucleotides or less, 500 nucleotides or less, 400 nucleotides or less, 300 nucleotides or less, 200 nucleotides or less, 100 nucleotides or less, 50 nucleotides or less, 30 nucleotides or less, or 20 nucleotides or less.

The term "CNS-10 sequence" refers to a long-range cis acting regulatory element located in the intergenic region between the OCTN1 gene and the RIL-gene. The CNS-10 sequence is highly conserved (e.g., greater than 70% identity) among mammals. For example, in human a CNS-10 sequence has a sequence of SEQ ID NO:10 and in mouse a CNS-10 sequence has a sequence of SEQ ID NO:26, wherein the two sequences share about 80% sequence identity. Accordingly, the term "CNS-10 sequence" refers to polymorphic variants, alleles, interspecies homologs, and mutants that: (1) have about 70% nucleotide sequence identity, preferably about 80% nucleotide sequence identity, more preferably about 90% nucleotide sequence identity, even more preferably about 95% nucleotide sequence identity or higher to SEQ ID NO:10 or to SEQ ID NO:26, over a window of about at least 50–100 nucleotides; (2) specifically hybridize (with a size of at least about 50 nucleotides, preferably at least about 100 nucleotides) under stringent hybridization conditions to a sequence selected from a group consisting of SEQ ID NO:10 and SEQ ID NO:26; or (3) are amplified by primers that specifically hybridize under stringent hybridization conditions to SEQ ID NO:10 or SEQ ID NO:26. The term "CNS-10 sequence" can refer to any sequence that have properties described above and can be of any length as long as it comprises binding sites for transcription factor(s). For example, CNS-10 sequence can refer to a nucleotide sequence having 1000 nucleotides or less, 500 nucleotides or less, 400 nucleotides or less, 300 nucleotides or less, 200 nucleotides or less, 100 nucleotides or less, 50 nucleotides or less, 30 nucleotides or less, or 20 nucleotides or less.

The term "CNS-11 sequence" refers to a long-range cis acting regulatory element located in the intergenic region between the Hs.13308 gene and the Septin2-homolog gene. The CNS-11 sequence is highly conserved (e.g., greater than 70% identity) among mammals. For example, in human a CNS-11 sequence has a sequence of SEQ ID NO:11 and in mouse a CNS-11 sequence has a sequence of SEQ ID NO:27, wherein the two sequences share about 81% sequence identity. Accordingly, the term "CNS-11 sequence" refers to polymorphic variants, alleles, interspecies homologs, and mutants that: (1) have about 70% nucleotide sequence identity, preferably about 80% nucleotide sequence identity, more preferably about 90% nucleotide sequence identity, even more preferably about 95% nucleotide sequence identity or higher to SEQ ID NO:11 or to SEQ ID NO:27, over a window of about at least 50–100 nucleotides; (2) specifically hybridize (with a size of at least about 50 nucleotides, preferably at least about 100 nucleotides) under stringent hybridization conditions to a sequence selected from a group consisting of SEQ ID NO:11 and SEQ ID NO:27; or (3) are amplified by primers that specifically hybridize under stringent hybridization conditions to SEQ ID NO:11 or SEQ ID NO:27. The term "CNS-11 sequence" can refer to any sequence that have properties described above and can be of any length as long as it comprises binding sites for transcription factor(s). For example, CNS-11 sequence can refer to a nucleotide sequence having 1000 nucleotides or less, 500 nucleotides or less, 400 nucleotides or less, 300 nucleotides or less, 200 nucleotides or less, 100 nucleotides or less, 50 nucleotides or less, 30 nucleotides or less, or 20 nucleotides or less.

The term "CNS-12 sequence" refers to a long-range cis acting regulatory element located in the intergenic region between the GDF 9 gene and the APX-homolog gene. The CNS-12 sequence is highly conserved (e.g., greater than 70% identity) among mammals. For example, in human a CNS-12 sequence has a sequence of SEQ ID NO:12 and in mouse a CNS-12 sequence has a sequence of SEQ ID NO:28, wherein the two sequences share about 84% sequence identity. Accordingly, the term "CNS-12 sequence" refers to polymorphic variants, alleles, interspecies homologs, and mutants that: (1) have about 70% nucleotide sequence identity, preferably about 80% nucleotide sequence identity, more preferably about 90% nucleotide sequence identity, even more preferably about 95% nucleotide sequence identity or higher to SEQ ID NO:12 or to SEQ ID NO:28, over a window of about at least 50–100 nucleotides; (2) specifically hybridize (with a size of at least about 50 nucleotides, preferably at least about 100 nucleotides) under stringent hybridization conditions to a sequence selected from a group consisting of SEQ ID NO:12 and SEQ ID NO:28; or (3) are amplified by primers that specifically hybridize under stringent hybridization conditions to SEQ ID NO:12 or SEQ ID NO:28. The term "CNS-12 sequence" can refer to any sequence that have properties described above and can be of any length as long as it comprises binding sites for transcription factor(s). For example, CNS-12 sequence can refer to a nucleotide sequence having 1000 nucleotides or less, 500 nucleotides or less, 400 nucleotides or less, 300 nucleotides or less, 200 nucleotides or less, 100 nucleotides or less, 50 nucleotides or less, 30 nucleotides or less, or 20 nucleotides or less.

The term "CNS-13 sequence" refers to long-range cis acting regulatory element located in the intergenic region between the LIM domain-pseudogene and the P4-hydroxylase alpha (II) gene. The CNS-13 sequence is highly conserved (e.g., greater than 70% identity) among mammals. For example, in human a CNS-13 sequence has a sequence of SEQ ID NO:13 and in mouse a CNS-13 sequence has a sequence of SEQ ID NO:29, wherein the two sequences share about 75% sequence identity. Accordingly, the term "CNS-13 sequence" refers to polymorphic variants, alleles, interspecies homologs, and mutants that: (1) have about 70% nucleotide sequence identity, preferably about 80% nucleotide sequence identity, more preferably about 90% nucleotide sequence identity, even more preferably about 95% nucleotide sequence identity or higher to SEQ ID NO:13 or to SEQ ID NO:29, over a window of about at least 50–100 nucleotides; (2) specifically hybridize (with a size of at least about 50 nucleotides, preferably at least about 100 nucleotides) under stringent hybridization conditions to a sequence selected from a group consisting of SEQ ID NO:13 and SEQ ID NO:29; or (3) are amplified by primers that specifically hybridize under stringent hybridization conditions to SEQ ID NO:13 or SEQ ID NO:29. The term "CNS-13 sequence" can refer to any sequence that have properties described above and can be of any length as long as it comprises binding sites for transcription factor(s). For example, CNS-13 sequence can refer to a nucleotide sequence having 1000 nucleotides or less, 500 nucleotides or less, 400 nucleotides or less, 300 nucleotides or less, 200 nucleotides or less, 100 nucleotides or less, 50 nucleotides or less, 30 nucleotides or less, or 20 nucleotides or less.

The term "CNS-14 sequence" refers to a long-range cis acting regulatory element located in the intergenic region between the Rad50 gene and the IL-5 gene. The CNS-14 sequence is highly conserved (e.g., greater than 70% identity) among mammals. For example, in human a CNS-14 sequence has a sequence of SEQ ID NO:14 and in mouse a CNS-14 sequence has a sequence of SEQ ID NO:30, wherein the two sequences share about 70% sequence identity. Accordingly, the term "CNS-14 sequence" refers to polymorphic variants, alleles, interspecies homologs, and mutants that: (1) have about 70% nucleotide sequence identity, preferably about 80% nucleotide sequence identity, more preferably about 90% nucleotide sequence identity, even more preferably about 95% nucleotide sequence identity or higher to SEQ ID NO:14 or to SEQ ID NO:30, over a window of about at least 50–100 nucleotides; (2) specifically hybridize (with a size of at least about 50 nucleotides, preferably at least about 100 nucleotides) under stringent hybridization conditions to a sequence selected from a group consisting of SEQ ID NO:14 and SEQ ID NO:30; or (3) are amplified by primers that specifically hybridize under stringent hybridization conditions to SEQ ID NO:14 or SEQ ID NO:30. The term "CNS-14 sequence" can refer to any sequence that have properties described above and can be of any length as long as it comprises binding sites for transcription factor(s). For example, CNS-14 sequence can refer to a nucleotide sequence having 1000 nucleotides or less, 500 nucleotides or less, 400 nucleotides or less, 300 nucleotides or less, 200 nucleotides or less, 100 nucleotides or less, 50 nucleotides or less, 30 nucleotides or less, or 20 nucleotides or less.

The term "CNS-15 sequence" refers to a long-range cis acting regulatory element located in the Hs.70932 region. The CNS-15 sequence is highly conserved (e.g., greater than 70% identity) among mammals. For example, in human a CNS-15 sequence has a sequence of SEQ ID NO:15 and in mouse a CNS-15 sequence has a sequence of SEQ ID NO:31, wherein the two sequences share about 82% sequence identity. Accordingly, the term "CNS-15 sequence" refers to polymorphic variants, alleles, interspecies homologs, and mutants that: (1) have about 70% nucleotide sequence identity, preferably about 80% nucleotide sequence identity, more preferably about 90% nucleotide sequence identity, even more preferably about 95% nucleotide sequence identity or higher to SEQ ID NO:15 or to SEQ ID NO:31, over a window of about at least 50–100 nucleotides; (2) specifically hybridize (with a size of at least about 50 nucleotides, preferably at least about 100 nucleotides) under stringent hybridization conditions to a sequence selected from a group consisting of SEQ ID NO:15 and SEQ ID NO:31; or (3) are amplified by primers that specifically hybridize under stringent hybridization conditions to SEQ ID NO:15 or SEQ ID NO:31. The term "CNS-15 sequence" can refer to any sequence that have properties described above and can be of any length as long as it comprises binding sites for transcription factor(s). For example, CNS-15 sequence can refer to a nucleotide sequence having 1000 nucleotides or less, 500 nucleotides or less, 400 nucleotides or less, 300 nucleotides or less, 200 nucleotides or less, 100 nucleotides or less, 50 nucleotides or less, 30 nucleotides or less, or 20 nucleotides or less.

The term "CNS-16 sequence" refers to a long-range cis acting regulatory element located in the P4-hydroxylase alpha (II) region. The CNS-16 sequence is highly conserved (e.g., greater than 70% identity) among mammals. For example, in human a CNS-16 sequence has a sequence of SEQ ID NO:16 and in mouse a CNS-15 sequence has a sequence of SEQ ID NO:32, wherein the two sequences share about 76% sequence identity. Accordingly, the term "CNS-16 sequence" refers to polymorphic variants, alleles, interspecies homologs, and mutants that: (1) have about 70% nucleotide sequence identity, preferably about 80% nucleotide sequence identity, more preferably about 90% nucleotide sequence identity, even more preferably about 95% nucleotide sequence identity or higher to SEQ ID NO:16 or to SEQ ID NO:32, over a window of about at least 50–100 nucleotides; (2) specifically hybridize (with a size of at least about 50 nucleotides, preferably at least about 100 nucleotides) under stringent hybridization conditions to a sequence selected from a group consisting of SEQ ID NO:16 and SEQ ID NO:32; or (3) are amplified by primers that specifically hybridize under stringent hybridization conditions to SEQ ID NO:16 or SEQ ID NO:32. The term "CNS-16 sequence" can refer to any sequence that have properties described above and can be of any length as long as it comprises binding sites for transcription factor(s). For example, CNS-16 sequence can refer to a nucleotide sequence having 1000 nucleotides or less, 500 nucleotides or less, 400 nucleotides or less, 300 nucleotides or less, 200 nucleotides or less, 100 nucleotides or less, 50 nucleotides or less, 30 nucleotides or less, or 20 nucleotides or less.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous.

"Nucleic acid" or "polynucleotide" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5× SSC, and 1% SDS, incubating at 42° C., or, 5× SSC, 1% SDS, incubating at 65° C., with wash in 0.2× SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1× SSC at 45° C. A positive hybridization is at least twice background. Those of ordinary skill will readily recognize that alternative hybridization and wash conditions can be utilized to provide conditions of similar stringency.

An "expression cassette" refers to a polynucleotide molecule comprising expression control sequences operatively linked to coding sequence(s).

A "vector" is a replicon in which another polynucleotide segment is attached, so as to bring about the replication and/or expression of the attached segment.

"Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term "control sequences" is intended to include, at a minimum, all components whose presence is necessary for expression, and may also include additional components whose presence is advantageous, for example, leader sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993)). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990)).

For preparation of monoclonal or polyclonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552–554 (1990); Marks et al., *Biotechnology* 10:779–783 (1992)).

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to fusion proteins can be selected to obtain only those polyclonal antibodies that are specifically immunoreactive with fusion protein and not with individual components of the fusion proteins. This selection may be achieved by subtracting out antibodies that cross-react with the individual antigens. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

Polynucleotides may comprise a native sequence (i.e., an endogenous sequence that encodes an individual antigen or a portion thereof) or may comprise a variant of such a sequence. Polynucleotide variants may contain one or more substitutions, additions, deletions and/or insertions such that the biological activity of the encoded chimeric protein is not diminished, relative to a chimeric protein comprising native antigens. Variants preferably exhibit at least about 70% identity, more preferably at least about 80% identity and most preferably at least about 90% identity to a polynucleotide sequence that encodes a native polypeptide or a portion thereof.

The terms "identical" or percent "identity," in the context of two or more nucleic acids or polypeptide sequences, refer to two or more sequences or subsequences that are the same or have a specified percentage of amino acid residues or nucleotides that are the same (i.e., 70% identity, optionally 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 25 to about 50 amino acids or nucleotides in length, or optionally over a region that is 75–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 25 to 500, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387–395 (1984)).

Another example of algorithm that is suitable for determining percent sequence identity and sequence similarity are the BLAST and BLAST 2.0 algorithms, which are described in Altschul et al., *Nuc. Acids Res.* 25:3389–3402 (1997) and Altschul et al., *J. Mol. Biol.* 215:403–410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of algorithm that is suitable for determining percent sequence identity and sequence similarity is Pipmaker algorithms, which can be found in published URLs, http://bio/cse.psu/edu/, and http://bio.cse.psu.edu/pipmaker. See also, Schwartz et al., *Genomic Res.* 10:577–586 (2000). Pipmaker computes alignments of similar regions in two DNA sequences, and the resulting alignments are summarized with a "percent identity plot, or "pip" for short. As described in the example section, alignments between two sequences can be computed with a dynamic programming method, scoring each nucleotide match as 1, each mismatch as −1, and each gap of length k as −6 to 0.2k. The percent identity displays a first sequence positions and the percent identity of each segment of the alignment between successive gaps that has a length of at least about 40 bp and at least about 60% identity.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally-occurring.

The term "subsequence" refers to a sequence of nucleic acids or amino acids that comprise a part of a longer sequence of nucleic acids or polypeptides, respectively.

The term "promoter" is a DNA sequence generally described as the 5'-region of a gene, located proximal to the start codon. The transcription of an adjacent DNA segment is initiated at the promoter region.

The term "recombination site sequences" refer to nucleic acid sequences that are recognized by a specific recombinase enzyme and allow exchange of DNA sequences at the site.

The term "recombinase" is an enzyme which catalyzes the exchange of DNA segments at specific recombination sites.

The term "transgenic" refers to a cell that includes a specific modification that was introduced into the cell, or an ancestor of the cell. Such modifications can include one or more point mutations, deletions, insertions, or combinations thereof. When referring to an animal, the term "transgenic" means that the animal includes cells that are transgenic. As used herein, transgenic can mean a piece of exogenous DNA that was introduced into a host nucleus, for example, human DNA introduced into a mouse nucleus. A genetically modified animal can either have alterations in its endogenous DNA or have foreign DNA (human transgenes) introduced into its genome (trangenic animals). Also, transgenic can also mean knockout animals wherein an endogenous gene in the chromosome is deleted. Thus, the term "transgenic" is used herein to refer to any genetically modified cell or animal.

BRIEF DESCRIPTION OF THE DRAWINGS

FIG. 2 illustrates cross-species sequence analysis of 15 conserved non-coding elements shown as Table 1.

FIGS. 3A–3C illustrate genomic structure and copy number analysis of the CNS-1$^{wt}$ and CNS-1$^{del}$ YAC transgenes. (A) Genomic structure of the CNS-1$^{wt}$ and CNS-1$^{del}$ YACs resulting from Cre-mediated loxP recombination in vivo (loxP sites flanking CNS-1 are depicted as black triangles). Positions of human probes (open boxes) used for Southern blot analyses and restriction enzyme fragments (blue bars) generated by Sph I (C), Bgl 11 (B) and Sac I (S) digests are shown. Probes 2 and 3 are located in approximately the same position upstream of IL-4 in the human and mouse genomes, respectively. (B) Southern blot analysis of CNS-1$^{wt}$ and CNS-1$^{del}$ transgenic mice investigating the genomic organization of the human IL-4/IL-13 region. Tail genomic DNA digested with Sph I and Bgl II was hybridized with probe 1. (C) Southern blot analysis used to determine YAC copy number in paired CNS-1$^{wt}$ and CNS-1$^{del}$ transgenic lines. Sac I digested tail genomic DNA was hybridized with human probe 2, and with mouse probe 3.

DETAILED DESCRIPTION

I. Introduction

Figure 1:
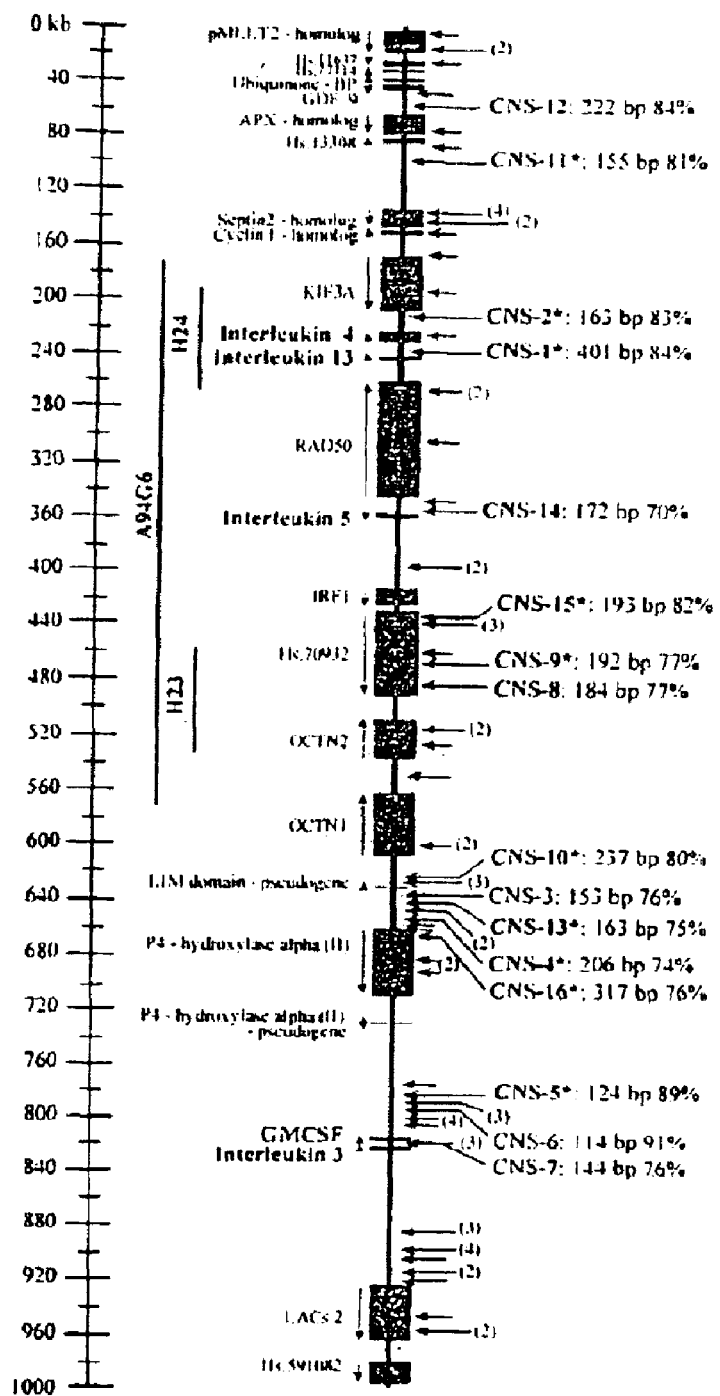
FIG. 1 illustrates physical map of the 1 Mb human 5q31 region. The locations of the 23 genes in the interval (7) (gray boxes), their direction of transcription, and the locations of all conserved non-coding sequences are shown. A number next to a horizontal arrow indicates that more than one conserved non-coding sequence was found at that location. The lengths and percent identities of the human/mouse alignments of the 15 non-coding sequences investigated in this study are given. The 12 elements determined to be single copy in the human genome are in bold. Non-coding sequences conserved in other vertebrates (Table 1) are marked (*). The locations of the human YAC (A94G6) and P1 clones (H23 and H24) (vertical bars) used in this study are shown.

The proper regulation of the expression of cytokines, such as IL-4, IL-5 and IL-13, is necessary to maintain human health. For example, genetic studies have established a linkage between the human 5q31 chromosomal region and asthma and atopic diseases seen in various populations. Postma et al., *N. Engl. J Med.* 333:894 (1995); Daniels et al., *Nature* 383:247 (1996) Analysis of transgenic mice strongly supports that the cytokine gene cluster regions contribute in establishing the asthma phenotype. Symula et al., *Nat. Genet.* 23:241 (1999). Also, the prevalence of $T_H2$ responses may play some role in a more rapid evolution of human immunodeficiency virus infection to the full-blown disease. Also, it is known that the classically allergic phenotype is characterized by eosinophilia and increased production of $T_H2$ cytokines.

Decreased production of IL-4 and related cytokines also carries negative health implications. These are described in, for example: (1) Singer & Nash, *T-cell-dependent control of acute Giardia lamblia infections in mice, Infect. Immun.* 68:170–175 (2000); (2) Mohrs et al., *Differences between IL-4-and IL-4 receptor alpha-deficient mice in chronic leishmaniasis reveal a protective role for IL-13 receptor signaling, J. Imm.* 162(12):7302 (1999); (3) Bancroft et al., *A critical role for IL-13 in resistance to intestinal nematode infection, J. Imm.* 160(7):3453–61 (1998).

The CNS sequences described herein may therefore be employed in various diagnostic tests to detect the presence of altered CNS sequences in test samples. The CNS sequences can also be employed in drug discovery assays to identify compounds that modulate the cytokine gene expression. These sequences may be altered genetically or may be altered by the administration of drugs that increase or decrease the binding of a cognate activator or repressor to the CNS sequences.

In embodiments of the invention, the CNS sequences can be used as a diagnostic tool for identifying subjects with diseases related to the cytokine gene expression. For example, a subject's DNA is tested for the presence, absence, mutation, or polymorphism in a CNS region of interest. This testing can be performed through the use of DNA test sequences (probes or primers) which are designed to hybridize to the region being tested. The DNA test sequences can be subsequences of the CNS sequences described herein. Their positive binding to the subject's DNA indicates a normal CNS sequence; the failure to bind under stringent conditions indicates the lack of a normal CNS sequence. Alternatively, the subject's CNS sequences can be sequenced using amplification techniques, such as PCR, to determine whether the subject has any mutations in the CNS sequences.

Moreover, the CNS sequences can be used in drug discovery assays. For example, in drug discovery assays, cell lines or bacterial strains are engineered to contain CNS sequences coupled to reporter genes. The CNS activity is turned on as described, and various test compounds are added to interfere with CNS activation. For example, antisense compounds or antibodies to the cognate binding protein of the CNS sequence are added as test compounds. The antibodies used may be antibody fragments, single chain antibodies, intrabodies (created from antibody DNA molecules), etc. Various assays which utilize transcription of a reported gene are described in U.S. Pat. No. 5,401,629 and U.S. Pat. No. 5,436,128, which are hereby incorporated by reference. Other uses for non-coding regulatory sequences are described in U.S. Pat. No. 5,776,776 and U.S. Pat. No. 5,922,596, which are hereby incorporated by references, and can be applied in embodiments of the present invention.

Moreover, transgenic animals described herein in connection with deleted or wild-type human CNS-1 sequences may be used in pharmaceutical studies to discover CNS-modulating drugs or biological agents. These animals may be engineered in accordance with the examples provided here with CNS sequences other than CNS-1. Also, knockout animals with deletion of mouse CNS sequences can be engineered for use in drug discovery. They serve as in vivo models for various therapeutic modalities suggested by the present work.

II. CNS Sequences and Their Isolation

A. CNS Sequences

In one aspect, the invention provides isolated CNS nucleic acid molecules that regulate expression of cytokine genes. As described above, among many non-coding sequences found in the 1-Mb human 5q31 chromosomal region, interspersed among different cytokine genes, sixteen different CNS sequences are identified and further characterized. The locations of the 23 genes and all of the 16 CNS sequences are shown in FIG. 1. Transcription factors bind to various CNS sequences and regulate the cytokine gene expression in a coordinate manner.

In one embodiment, the isolated CNS nucleic acid molecule is a CNS-1 sequence. The CNS-1 sequence is located in the intergenic region between the IL-4 gene and the IL-13 gene. As described in the example section below, the CNS-1 sequence regulates three genes, IL-4, IL-13 and IL-5 which are spread over 120 kilobases. For example, the presence of human CNS-1 sequence in transgenic mice increases the number of $T_H2$ cells that express IL-4 and IL-13. The presence of human CNS-1 sequence in transgenic mice increases the production of human IL-5 gene. Also, according to CNS-1 knockout mice studies, CNS-1 is also has a mild enhancer activity. The deletion of endogenous CNS-1 sequence from the mouse chromosome reduces the net expression of IL-4, IL-13 and IL-5 mRNA or proteins.

Examples of CNS-1 sequences include those that are isolated from the intergenic region between the IL-4 gene and IL-13 gene from vertebrate species. In one embodiment, a CNS-1 sequence is derived from the human 5q31 chromosomal region and has SEQ ID NO:1 or a subsequence thereof. In another embodiment, a CNS-1 sequence is derived from mouse and has SEQ ID NO:17 or a subsequence thereof. In another embodiment, a CNS-1 sequence is derived from mouse and has a reverse complement sequence of SEQ ID NO:34 or a subsequence thereof. In another embodiment, a CNS-1 sequence is derived from rat and has a reverse complement sequence of SEQ ID NO:35 or a subsequence thereof. In another embodiment, a CNS-1 sequence is derived from rabbit and has a reverse complement sequence of SEQ ID NO:36 or a subsequence thereof. In another embodiment, a CNS-1 sequence is derived from dog and has a reverse complement sequence of SEQ ID NO:37 or a subsequence thereof. In another embodiment, a CNS-1 sequence is derived from cow and has a reverse complement sequence of SEQ ID NO:38 or a subsequence thereof. The CNS-1 sequences derived from these mammals share a high degree of sequence identity (see FIG. 2). Accordingly, embodiments of the invention also include CNS-1 sequences that are at least about 70% identical, optionally at least about 80% identical, optionally at least about 90% identical, optionally at least about 95% identical or any integer between 70% to 99% identical to SEQ ID NO:1 or SEQ ID NO:17.

In another embodiment, the isolated CNS nucleic acid molecule is a CNS-2 sequence. The CNS-2 sequence is located in the intergenic region between the KIF3A gene and the IL-4 gene. The CNS-2 sequence from the human 5q31 chromosomal region is shown in SEQ ID NO:2. The CNS-2 sequence from mouse chromosome 11 is shown in SEQ ID NO:18. The CNS-2 demonstrates a high degree of conservation across mammals (see FIG. 2). Accordingly, embodiments of the invention also include CNS-2 sequences that are at least about 70% identical, optionally at least about 80% identical, optionally at least about 90% identical, optionally at least about 95% identical or any integer between 70% to 99% identical to SEQ ID NO:2 or SEQ ID NO:18.

In another embodiment, the isolated CNS nucleic acid molecule is a CNS-3 sequence. The CNS-3 sequence is located about 2–3 kilobases upstream of the RIL gene. The CNS-3 sequence from the human 5q31 chromosomal region is shown in SEQ ID NO:3. The CNS-3 sequence from mouse chromosome 11 is shown in SEQ ID NO:19. The CNS-3 demonstrates a high degree of conservation across mammals (see FIG. 2). Accordingly, embodiments of the invention also include CNS-3 sequences that are at least about 70% identical, optionally at least about 80% identical, optionally at least about 90% identical, optionally at least about 95% identical or any integer between 70% to 99% identical to SEQ ID NO:3 or SEQ ID NO:19.

In another embodiment, the isolated CNS nucleic acid molecule is a CNS-4 sequence. The CNS-4 sequence is located in the intergenic region between the RIL gene and the P4-hydroxylase alpha (II) gene. The CNS-4 sequence from the human 5q31 chromosomal region is shown in SEQ ID NO:4. The CNS-4 sequence from mouse chromosome 11 is shown in SEQ ID NO:20. The CNS-4 demonstrates a high degree of conservation across mammals (see FIG. 2). Accordingly, embodiments of the invention also include CNS-4 sequences that are at least about 70% identical, optionally at least about 80% identical, optionally at least about 90% identical, optionally at least about 95% identical or any integer between 70% to 99% identical to SEQ ID NO:4 or SEQ ID NO:20.

In another embodiment, the isolated CNS nucleic acid molecule is a CNS-5 sequence. The CNS-5 sequence is located in the intergenic region between the P4-hydroxylase alpha (II) gene and the GMCSF gene: The CNS-5 sequence from the human 5q31 chromosomal region is shown in SEQ ID NO:5. The CNS-5 sequence from mouse chromosome 11 is shown in SEQ ID NO:21. The CNS-5 demonstrates a high degree of conservation across mammals (see FIG. 2). Accordingly, embodiments of the invention also include CNS-5 sequences that are at least about 70% identical, optionally at least about 80% identical, optionally at least about 90% identical, optionally at least about 95% identical or any integer between 70% to 99% identical to SEQ ID NO:5 or SEQ ID NO:21.

In another embodiment, the isolated CNS nucleic acid molecule is a CNS-6 sequence. The CNS-6 sequence is located in the intergenic region between the GMCSF gene and the IL-3 gene. The CNS-6 sequence from the human 5q31 chromosomal region is shown in SEQ ID NO:6. The CNS-6 sequence from mouse chromosome 11 is shown in SEQ ID NO:22. The CNS-6 demonstrates a high degree of conservation across mammals (see FIG. 2). Accordingly, embodiments of the invention also include CNS-6 sequences that are at least about 70% identical, optionally at least about 80% identical, optionally at least about 90% identical, optionally at least about 95% identical or any integer between 70% to 99% identical to SEQ ID NO:6 or SEQ ID NO:22.

In another embodiment, the isolated CNS nucleic acid molecule is a CNS-7 sequence. The CNS-7 sequence is located in the intergenic region between the GMCSF gene and the IL-3 gene. The CNS-7 sequence from the human 5q31 chromosomal region is shown in SEQ ID NO:7. The CNS-7 sequence from mouse chromosome 11 is shown in SEQ ID NO:23. The CNS-7 demonstrates a high degree of conservation across mammals (see FIG. 2). Accordingly, embodiments of the invention also include CNS-7 sequences that are at least about 70% identical, optionally at least about 80% identical, optionally at least about 90% identical, optionally at least about 95% identical or any integer between 70% to 99% identical to SEQ ID NO:7 or SEQ ID NO:23.

In another embodiment, the isolated CNS nucleic acid molecule is a CNS-8 sequence. The CNS-8 sequence is located in the Hs.70932 region. The CNS-8 sequence from the human 5q31 chromosomal region is shown in SEQ ID NO:8. The CNS-8 sequence from mouse chromosome 11 is shown in SEQ ID NO:24. The CNS-8 demonstrates a high degree of conservation across mammals (see FIG. 2). Accordingly, embodiments of the invention also include CNS-8 sequences that are at least about 70% identical, optionally at least about 80% identical, optionally at least about 90% identical, optionally at least about 95% identical or any integer between 70% to 99% identical to SEQ ID NO:8 or SEQ ID NO:24.

In another embodiment, the isolated CNS nucleic acid molecule is a CNS-9 sequence. The CNS-9 sequence is located in the Hs.70932 region. The CNS-9 sequence from the human 5q31 chromosomal region is shown in SEQ ID NO:9. The CNS-9 sequence from mouse chromosome 11 is shown in SEQ ID NO:25. The CNS-9 demonstrates a high degree of conservation across mammals (see FIG. 2). Accordingly, embodiments of the invention also include CNS-9 sequences that are at least about 70% identical, optionally at least about 80% identical, optionally at least about 90% identical, optionally at least about 95% identical or any integer between 70% to 99% identical to SEQ ID NO:9 or SEQ ID NO:25.

In another embodiment, the isolated CNS nucleic acid molecule is a CNS-10 sequence. The CNS-10 sequence is located in the intergenic region between the OCTN1 gene and the RIL gene. The CNS-10 sequence from the human 5q31 chromosomal region is shown in SEQ ID NO:10. The CNS-10 sequence from mouse chromosome 11 is shown in SEQ ID NO:26. The CNS-10 demonstrates a high degree of conservation across mammals (see FIG. 2). Accordingly, embodiments of the invention also include CNS-10 sequences that are at least about 70% identical, optionally at least about 80% identical, optionally at least about 90% identical, optionally at least about 95% identical or any integer between 70% to 99% identical to SEQ ID NO:10 or SEQ ID NO:26.

In another embodiment, the isolated CNS nucleic acid molecule is a CNS-11 sequence. The CNS-11 sequence is located in the intergenic region between the Hs.13308 gene and the Septin2-homolog gene. The CNS-11 sequence from the human 5q31 chromosomal region is shown in SEQ ID NO:11. The CNS-11 sequence from mouse chromosome 11 is shown in SEQ ID NO:27. The CNS-11 demonstrates a high degree of conservation across mammals (see FIG. 2). Accordingly, embodiments of the invention also include CNS-11 sequences that are at least about 70% identical, optionally at least about 80% identical, optionally at least about 90% identical, optionally at least about 95% identical or any integer between 70% to 99% identical to SEQ ID NO:11 or SEQ ID NO:27.

In another embodiment, the isolated CNS nucleic acid molecule is a CNS-12 sequence. The CNS-12 sequence is located in the intergenic region between the GDF 9 gene and the APXL-homolog gene. The CNS-12 sequence from the human 5q31 chromosomal region is shown in SEQ ID NO:12. The CNS-12 sequence from mouse chromosome 11 is shown in SEQ ID NO:28. The CNS-12 demonstrates a high degree of conservation across mammals (see FIG. 2). Accordingly, embodiments of the invention also include CNS-12 sequences that are at least about 70% identical, optionally at least about 80% identical, optionally at least about 90% identical, optionally at least about 95% identical or any integer between 70% to 99% identical to SEQ ID NO:12 or SEQ ID NO:28.

In another embodiment, the isolated CNS nucleic acid molecule is a CNS-13 sequence. The CNS-13 sequence is located in the intergenic region between the RIL gene and the P4-hydroxylase alpha (II) gene. The CNS-13 sequence from the human 5q31 chromosomal region is shown in SEQ ID NO:13. The CNS-13 sequence from mouse chromosome 11 is shown in SEQ ID NO:29. The CNS-13 demonstrates a high degree of conservation across mammals (see FIG. 2). Accordingly, embodiments of the invention also include CNS-13 sequences that are at least about 70% identical, optionally at least about 80% identical, optionally at least about 90% identical, optionally at least about 95% identical or any integer between 70% to 99% identical to SEQ ID NO:13 or SEQ ID NO:29.

In another embodiment, the isolated CNS nucleic acid molecule is a CNS-14 sequence. The CNS-14 sequence is located in the intergenic region between the Rad50 gene and the IL-5 gene. The CNS-14 sequence from the human 5q31 chromosomal region is shown in SEQ ID NO:14. The CNS-14 sequence from mouse chromosome 11 is shown in SEQ ID NO:30. The CNS-14 demonstrates a high degree of conservation across mammals (see FIG. 2). Accordingly, embodiments of the invention also include CNS-14 sequences that are at least about 70% identical, optionally at least about 80% identical, optionally at least about 90% identical, optionally at least about 95% identical or any integer between 70% to 99% identical to SEQ ID NO:14 or SEQ ID NO:30.

In another embodiment, the isolated CNS nucleic acid molecule is a CNS-15 sequence. The CNS-15 sequence is located in the Hs.70932 region. The CNS-15 sequence from the human 5q31 chromosomal region is shown in SEQ ID NO:15. The CNS-15 sequence from mouse chromosome 11 is shown in SEQ ID NO:31. The CNS-15 demonstrates a high degree of conservation across mammals (see FIG. 2). Accordingly, embodiments of the invention also include CNS-15 sequences that are at least about 70% identical, optionally at least about 80% identical, optionally at least about 90% identical, optionally at least about 95% identical or any integer between 70% to 99% identical to SEQ ID NO:15 or SEQ ID NO:31.

In another embodiment, the isolated CNS nucleic acid molecule is a CNS-16 sequence. The CNS-16 sequence is located in the P4-hydroxylase alpha (II) region. The CNS-16 sequence from the human 5q31 chromosomal region is shown in SEQ ID NO:16. The CNS-16 sequence from mouse chromosome 11 is shown in SEQ ID NO:32. The CNS-16 demonstrates a high degree of conservation across mammals (see FIG. 2). Accordingly, embodiments of the invention also include CNS-16 sequences that are at least about 70% identical, optionally at least about 80% identical, optionally at least about 90% identical, optionally at least about 95% identical or any integer between 70% to 99% identical to SEQ ID NO:16 or SEQ ID NO:32.

B. Methods for Isolation of CNS Sequences

The CNS sequences of the invention can be obtained using methods that are known to those of skill in the art. Suitable nucleic acids (e.g., genomic or subsequences (probes)) can be cloned, or amplified by in vitro methods such as the polymerase chain reaction (PCR), the ligase chain reaction (LCR), the self-sustained sequence replication system (SSR). A wide variety of cloning and in vitro amplification methodologies are well-known to persons of skill. Examples of these techniques and instructions sufficient to direct persons of skill through many cloning exercises are found in Berger & Kimmel, *Guide to Molecular Cloning Techniques, Methods in Enzymology* 152 Academic Press, Inc., San Diego, Calif. (Berger); Sambrook et al., *Molecular Cloning—A Laboratory Manual* (2nd ed.) Vol. 1–3, Cold Spring Harbor Laboratory, Cold Spring Harbor Press, NY (1989); *Current Protocols in Molecular Biology*, Ausubel et al., eds., Current Protocols, a joint venture between Greene Publishing Associates, Inc. and John Wiley & Sons, Inc., (1994 Supplement); Cashion et al., U.S. Pat. No. 5,017,478; and Carr, European Patent No. 0,246,864. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson *C&EN* 36–47 (Oct. 1, 1990); *The Journal Of NIH Research* 3: 81–94 (1991); Kwoh et al. *Proc. Natl. Acad. Sci. USA* 86: 1173 (1989); Guatelli et al, *Proc. Natl. Acad. Sci. USA* 87 (1990), 1874; Lomell et al.,*J. Clin. Chem.,* 35: 1826 (1989); Landegren et al., *Science* 241: 1077–1080 (1988); Van Brunt, *Biotechnology* 8: 291–294 (1990); Wu & Wallace, *Gene* 4: 560 (1989); and Barringer et al., *Gene* 89: 117 (1990). Improved methods of cloning in vitro amplified nucleic acids are described in Wallace et al., U.S. Pat. No. 5,426,039.

The CNS sequences of the invention, or subsequences thereof can be obtained using any suitable method as described above, including, for example, cloning and restriction of appropriate sequences. In cloning methods, a known nucleotide sequence of CNS sequences, such as those described herein, can be used to provide probes that specifically hybridize to other CNS nucleic acid sequences. Preferably, high stringent hybridization conditions are used to obtain other CNS sequences. Preferably, the samples are obtained from mammals, such as human, mouse, rat, cow, dog, pig, rabbit, etc., and the genomic DNA obtained from the samples are used to obtain other CNS nucleic acid sequences.

The CNS nucleic acid sequences or subsequences thereof can also be cloned using DNA amplification methods such as polymerase chain reaction (PCR). For example, the CNS nucleic acid sequence or subsequence thereof is PCR amplified, preferably using a sense primer containing one restriction site (e.g., XbaI) and an antisense primer containing another restriction site (e.g., HindIII). This will produce CNS sequences having terminal restriction sites. This nucleic acid can then be ligated into a vector containing a nucleic acid encoding the second molecule and having the appropriate corresponding restriction sites. Suitable PCR primers can be determined by one of skill in the art using the sequence information provided herein. Examples of suitable primers for amplification of CNS nucleic acid sequences are provided in the example section below. Amplified CNS sequences can be ligated into an appropriate vector for amplification and/or expression according to standard methods.

As an alternative to cloning CNS sequences, CNS sequences can be chemically synthesized from known sequences of CNS sequences of the invention (e.g., SEQ ID NOS:1 through 32). Direct chemical synthesis methods include, for example, the phosphotriester method of Narang et al., *Meth. Enzymol* 68: 90–99 (1979); the phosphodiester method of Brown et al., *Meth. Enzymol.* 68: 109–151 (1979); the diethylphosphoramidite method of Beaucage et al., *Tetra. Lett.,* 22: 1859–1862 (1981); and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is often limited to sequences of about 100 bases, longer sequences may be obtained by the ligation of shorter sequences. Alternatively, subsequences may be cloned and the appropriate subsequences cleaved using appropriate restriction enzymes. The fragments can then be ligated to produce the desired DNA sequence.

In some embodiments, it may be desirable to modify the CNS sequences. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman & Smith, *Gene* 8:81–97 (1979); Roberts et al., *Nature* 328: 731–734 (1987).

C. Methods for Identifying Binding Sites of Transcription Factors in CNS Sequences and Methods for Identifying Transcription Factors Any suitable methods known in the art can be used to identify binding sites of transcription factors within CNS sequences. For example, a gel-mobility shift assay can be used. As an illustration, a CNS sequence is cleaved into shorter subsequences of specific length and sequence. These subsequences are labeled (e.g., radiolabeled) and incubated with cellular extracts, e.g., from T cells. The incubation is performed under conditions which allow the formation of protein-DNA complexes. Protein-DNA complexes are resolved from uncomplexed DNA by electrophoresis through polyacrylamide gels in low ionic strength buffers. In order to minimize binding of protein in a sequence nonspecific fashion, a competitor DNA species can be added to the incubation mixture of the extract and DNA probe. Proteins bound to a CNS sequence will cause it to move more slowly through the gel. If a CNS subsequence corresponds to a chromosome region where transcription factors bind, autoradiography will reveal a series of bands. This subsequence, to which transcription factor(s) bind, can be identified by, e.g., sequencing. See, e.g., Ausubel et al., supra.

In another example, genetic footprinting can be used to identify binding sites of transcription factors. One type of genetic footprinting that can be used is DNase I protection mapping. In this procedure, protein is first bound to DNA and then the DNA is cleaved either by DNase or chemical agents. DNase footprinting typically reveals the general region(s) of DNA to which a protein binds. See, e.g., Ausubel et al., supra; Mellott et al., *Am. J. Physiol. Lung Cell Mol. Physiol.* 280(3):L390–L399 (2001); Hare et al., *J. Bacteriol.* 183(5):1694–1706 (2001).

In another example, an in vivo method, such as in vivo crosslinking and immunoprecipitation with antibodies directed to transcription factors can be used to identify the proteins that influence CNS functions. These methods are described in, e.g., *Methods Mol. Biol.* 119:497–508 (1999); Toth, *Nucleic Acids Res.* 28(24):e4 (2000).

In another method, computational analysis of transcription factor binding sites can be performed using profile weight matrices. For example, Transcription factor database searches can be performed using TRANSFAC http://transfac.gbf.de/TRANSFAC/index.html. See, also, Wingender et al., *Nucleic Acids Res.* 28:316–319 (2000).

The above-described methods and other methods known in the art can also be used to identify transcription factors which bind to CNS sequences. Moreover, DNA affinity chromatography can be used to isolate transcription factors. In this technique, a double-stranded CNS sequence is provided and linked to an insoluble porous matrix, such as agarose. Then the matrix is used to construct a column that selectively binds proteins that recognize the particular DNA sequence. Then the proteins can be eluted from the matrix, and their identity can be determined. See, e.g., Ausubel et al., supra.

III. Expression Cassettes and Vectors Comprising CNS Sequences

In another aspect, the invention provides expression cassettes and vectors comprising CNS sequences that can be used, e.g., to express cytokine genes or other heterologous coding sequences, such as reporter genes driven by cytokine gene promoters or heterologous promoters). These constructs can be used to transfect host cells or to make transgenic animals to further characterize CNS sequences or to assay for compounds that modulate binding of transcription factors to CNS sequences.

A. Expression Cassette Comprising CNS-Sequence and Reporter Gene

In one embodiment, expression cassettes comprising a reporter gene and a CNS sequence are provided. These reporter gene constructs are prepared by linking a heterologous coding sequence to a promoter which controls transcription of a heterologous coding sequence, and the constructs further comprise a CNS sequence which is operably linked to the promoter. These expression cassettes are useful, among others, to screen compounds which modulate binding of transcription factors to CNS sequences or other functions of CNS sequences. In a preferred embodiment, the CNS sequence is a CNS-1 sequence from human or mouse having SEQ ID NO:1 or SEQ ID NO:17, respectively, or subsequences thereof.

The CNS-1 sequence can be located positioned in any suitable location within the expression cassette as long as its regulatory functions can be monitored via transcription of the reporter genes. For example, the CNS-1 sequence can be located several kilobases (e.g., 20 kilobases, 10 kilobases, 5 kilobases, 3 kilobases) away from the promoter of the heterologous coding sequence. As shown in the Example section below, although the CNS-1 sequence is over 100 kilobases away from the IL-5 gene, it can still regulate the IL-5 gene expression. Typically, however, given the constraints of insert size for many vectors, the CNS-1 sequence is located within, e.g., 5 kilobases, 3 kilbases, or 1 kilobases from the promoter, more typically within 500 bases, 100 bases or 50 bases from the promoter which controls the transcription of a heterologous coding sequence.

The heterologous coding sequence is typically a reporter gene that expresses a detectable gene product, which may be RNA or protein. Preferred genes are those that are readily detectable. The reporter gene may also be included in the construct in the form of a fusion protein with a gene that includes desired transcriptional regulatory sequences (e.g., cytokine genes, such as IL-4, IL-13 or IL-5 genes). Examples of reporter genes include a chloramphenicol acetyltransferase gene, a firefly luciferase gene, a bacterial luciferase gene, a β-galactosidase gene or an alkaline phosphatase gene, a gene that encodes fluorescent proteins such as green fluorescent protein (GFP).

Any suitable promoters and optionally other transcription regulatory elements can be included in the expression cassette. The promoter is preferably positioned about the same distance from the heterologous coding sequence transcription start site as it is from the transcription start site in its natural setting. As is known in the art, however, some variation in this distance can be accommodated without loss of promoter function. The promoter can be constitutive or inducible, heterologous or homologous. Preferably, the promoters that are activatable in T cells, e.g., $T_H1$ cells, $T_H2$ cells, $T_H0$ cells, mast cells, or eosinophils. These promoters include, SV40, IL-4, IL-13, IL-5, IL-2, interferron gamma, $T_H1$ and $T_H2$ cytokine promoters, inducible promoters such as tetracyclin inducible promoters. More preferably, the transcription regulatory elements including the promoters are derived from cytokine genes, such as IL-4, IL-13 and IL-5.

The expression cassette further comprises other elements required for the expression of the reporter gene in the host cells. These other elements include, e.g., signals required for efficient polyadenylation of the transcript and translation termination sequences for efficient termination. The termination sequences may be obtained from the same gene as the promoter sequence or may be obtained from different genes, preferably from cytokine genes. The heterologous coding sequence may also be linked to a cleavable signal peptide sequence to promote secretion of the encoded protein by the transformed cells. Cleavable signal peptide sequences are well-known in the art, and the selection of suitable signal peptide sequences is well within the skill of those in the art.

In some embodiments, expression cassettes may comprise a portion of the human 5q31 chromosomal region or a portion of mouse chromosome 11 containing at least one cytokine gene and at least one CNS sequence, wherein one or more cytokine genes, such as IL-4, IL-13 and/or IL-5, are substituted by reporter gene(s). If more than one cytokine genes are substituted with reporter genes, then preferably different reporter genes are substituted for the cytokine genes. These expression cassettes provide means for the CNS sequences to regulate the reporter gene expression in their natural environment.

B. Expression Cassette Comprising Cytokine Genes and CNS Sequences

In another embodiment, an expression cassette comprises one or more cytokine genes and at least one CNS sequence. For example, an expression cassette may comprise or consist essentially of an IL-4 gene, an IL-13 gene and a CNS-1 sequence. In another example, an expression cassette may comprise or consist essentially of an IL-4 gene, an IL-13 gene, an IL-5 gene, and a CNS-1 sequence. Such expression cassettes have many utilities. For example, the expression cassette can be used to obtain cytokine proteins by introducing the expression cassette in host cells in vitro or in transgenic animals. In another example, the expression cassette can be used to find compounds that modulate the binding of transcription factors to CNS sequences.

In expression cassettes, cytokine genes and CNS sequences can be arranged in any suitable manner so that at least one CNS sequence regulates at least one cytokine gene within the expression cassette. For example, a CNS sequence is located within 1 kilobases, more typically within 500 bases, even more typically within 100 or 50 bases from a cytokine gene promoter. Any suitable promoters and other regulatory elements can be used in embodiments of the invention. Examples of promoters and other regulatory elements that can be included in expression cassettes are described above, and will not be repeated in this section.

In some embodiments, the expression cassette comprises a portion of the human 5q31 chromosomal region or mouse chromosome 11, and the cytokine genes and CNS sequences are located in their native organization within the expression cassette. Such expression cassettes are particularly useful in producing non-human transgenic animals using vectors such as YAC, which can accommodate large inserts.

C. Expression Cassette Comprising Cytokine Gene and Lacking CNS Sequence

In another embodiment, an expression cassette comprises one or more cytokine genes but lacks one or more CNS sequences. In a preferred embodiment, at least a CNS-1 sequence is omitted from the expression cassette. For example, an expression cassette comprises an IL-4 gene, an IL-13 gene, but lacks a CNS-1 sequence. In another example, an expression cassette comprises an IL-4 gene, an IL-13 gene and IL-5 gene, but lacks a CNS-1 sequence. Such expression cassettes are particularly useful in performing control experiments for evaluating the regulatory functions of CNS sequences on cytokine genes.

In expression cassettes, any suitable promoters and other regulatory elements can be used in embodiments of the invention. Examples of promoters and other regulatory elements that can be included in expression cassettes are described above, and will not be repeated in this section.

In some embodiments, the expression cassette comprises a portion of the human 5q31 chromosomal region which has a deletion of at least one CNS sequence, and the cytokine genes and CNS sequences, if present, are located within the region in their native organization. Preferably, the CNS-1 sequence is partially or fully deleted. Such expression cassettes are particularly useful in producing non-human transgenic animals using vectors such as YAC. Cells derived from such transgenic animal can be used as a control to compare the effect of absence of CNS sequences in cytokine gene expression to the effect of presence of CNS sequences in cytokine gene expression.

In other embodiments, the expression cassette may comprise a portion of mouse chromosome 11 comprising one or more cytokine genes and has a disruption in one or more CNS sequences. For example, selectable marker gene(s) may replace one or more CNS sequences in the portion of mouse chromosome 11. A selectable marker gene can be any gene that produces proteins that allows one to select for or against a cell that contains it (e.g., antibiotic resistance genes). In another example, the expression cassette may comprise a mutated version of a CNS sequence which does not allow binding of transcription factors that normally bind to the CNS sequence. Such expression cassettes can be used to produce knock-out transgenic animals, in which one or more endogenous CNS sequences in the chromosome are disrupted.

D. Expression Cassettes Comprising Cytokine Gene and CNS Sequence Flanked Between Two Recombination Site Sequences In another embodiment, an expression cassette comprises an IL-4 gene, an IL-13 gene, and a CNS-1 sequence flanked between two recombination site sequences. Recombination site sequences refer to nucleic acid molecules that are recognized by specific recombinase enzymes. Recombinase enzymes (along with associated proteins in some cases) recognize specific sequences of bases in DNA and exchange the DNA segments flanking those segments. Such expression cassettes allow in vitro or in vivo insertion or modification of genomic sequences. In particular, such expression cassettes can be used to make a pair of non-human transgenic animal which are identical, except one has a portion of the human 5q31 chromosomal region with a CNS sequence and other has a portion of the human 5q31 chromosome region lacking the CNS sequences.

Any suitable recombination site sequences can be used in embodiments of the invention. These include, e.g., loxP, attB, attP, attL, attR sequences, or flip-recombinase sites from Drosophila. LoxP is a 34 base pair sequence comprised of two 13 base pair inverted repeats (which serve as the recombinase binding sites) flanked by 8 base pair core sequence. Sauer, *Curr. Opin. Biotech.* 5:521–527 (1994). LoxP sequence is recognized by Cre recombinase. AttB, attP, attL and attR sequences are recognized by recombinase enzyme λ Integrase. AttB is an approximately 25 base pair sequence and contain two 9 base pair core-type Int binding sites and a 7 base pair overlap region. AttP is an approximately 240 base pair sequence and contain core-type Int binding sites and arm-type Int binding site as well as other protein binding sites. Landy, *Curr. Opin. Biotech.* 3:699–707 (1993). Any of these or other suitable recombination sites can be used to flank CNS sequences of the present invention.

In a preferred embodiment, the recombination site sequences are loxP site sequences. As shown in the example section below, loxP sites can be inserted into a YAC vector comprising a portion of human 5q31 region, wherein the loxP sites flank a CNS sequence, such as CNS-1. Then the YAC vector is introduced into the genome of a non-human animal. To delete the CNS-1 element, these transgenic animals are bred with transgenic animals expressing a Cre recombination transgene. Cre is a recombinase that catalyzes the exchange of DNA segments at the loxP sites. This results in the generation of two lines of transgenic animals, one with a CNS-1 containing YAC transgene and other with a YAC transgene in which the CNS-1 element had been deleted. Recombination site sequences, therefore, allow the production of paired CNS-1$^{wt}$ and CNS-1$^{del}$ transgenic animals that are genetically identical in every aspect, except for the presence or absence of the CNS-1 sequence. The production of paired transgenic animals are particularly useful in further characterizing the function of CNS sequences as well as in assays for identifying compounds that modulate the cytokine gene expression through influencing CNS sequences.

E. Vectors Comprising the Expression Cassettes

Any of the above described expression cassettes can be included into vectors to introduce the expression cassettes into host cells. The particular vector used to introduce the expression cassette into the host cell is not critical, and any conventional vectors can be used for expression in eukaryotic or prokaryotic cells. Expression vectors useful in embodiments of the invention include viral vectors such as retroviruses, adenoviruses and adeno-associated viruses, plasmid vectors, cosmids, and the like. Viral and plasmid vectors are preferred for transfecting mammalian cells. Various viral and plasmid vectors are commercially available and known in the art.

The vectors typically comprise selective marker genes to allow selection of host cells that have been transformed with a plasmid or a vector. These marker genes encode a protein necessary for the survival or growth of transformed host cells grown in selective culture medium. Host cells not transformed with the vector containing the selective gene will not survive in the culture medium. Typical selection genes encode proteins that confer resistance to antibiotics or other toxins, such as erythromycin, clindamycin, ampicillin, neomycin, kanamycin, penicillin, cetoxifin, imiprenen, metronidazole, streptomycin, chloramphenicol, or tetracycline. Alternatively, a selective marker may encode proteins that complement auxotrophic deficiencies or supply critical nutrients not available from complex media. A number of other selective markers are known to those skilled in the art and are described, for instance, in Sambrook et al., supra.

In some embodiments, yeast artificial chromosome ("YAC") cloning vectors are used to introduce cytokine genes and CNS sequences into host cells or to make non-human transgenic animals. YAC vectors are capable of propagating large cloned insert, 50 to more than 1000 kilobases, of nucleic acids. YAC cloning vectors are particularly useful for isolating large genes and intergenic sequences, such as the human 5q31 chromosomal region comprising cytokine genes and CNS sequences. YAC cloning is also useful for making vectors for performing homologous recombination in mammalian cells. For example, the above-described expression cassette comprising cytokine genes and a CNS sequence flanked between two recombination site sequences is typically inserted into YAC cloning vectors. Methods for manipulating YAC cloning vectors are well-known in the art, and are described in, e.g., U.S. Pat. No. 5,981,175. Other vectors, such as mammalian artificial chromosome (MAC) vector, can also be used to introduce large inserts and are described in, e.g., U.S. Pat. No. 6,133,503.

IV. Host Cells Comprising Expression Cassettes

A number of host cells can be used for transformation with the vectors of the invention. Preferably, host cells are mammalian cells, such as mouse or human cells. More preferably, host cells are T cells which can be stimulated to differentiate into $T_H1$ or $T_H2$ phenotypes. More preferably, T cells are stimulated to differentiate into $T_H2$ phenotype. The cells that can be differentiated into $T_H2$ phenotype include, e.g., the human Jurkat cell line, the mouse EL4 T cell line, D-5 and D-10, macrophage cell lines, and mast cell cell lines. The host cells can be transformed with the vectors using standard methods appropriate to such cells. These methods include, e.g., electroporation, microinjection calcium chloride method, polyethylene glycol method, etc. After vectors are introduced into host cells, the transfected cells are cultured under appropriate conditions. Cells containing the vectors can be selected by, e.g., resistance to antibiotics conferred by genes contained in the vector.

In some embodiments, primary cell cultures from transgenic animals can be isolated, and the cells can be induced into either $T_H1$ or $T_H2$ phenotypes. For example, T cells can be isolated from spleens and mesenteric lymph nodes of transgenic mice described herein. Transgenic animals can be those that are transformed with expression cassettes of the present invention. The methods for producing transgenic animals are described in detail below.

T cells then can be stimulated in vitro under conditions that favor development of either $T_H1$ or $T_H2$ cells. For example, cells can be activated using irradiated antigen-presenting cells with monoclonal antibodies against β T cell receptor and CD28 with IL-2; for $T_H1$ conditions, recombinant murine IL-12 and antibody to IL-4 can be used, and for $T_H2$ conditions, recombinant murine IL-4 can be used.

If desired, the polypeptides that are expressed by the host cells can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification*, Academic Press, Inc. N.Y. (1990)).

V. Non-Human Transgenic Animals

In another aspect, embodiments of the invention provide non-human transgenic animals comprising expression cassettes of the invention. For example, the transgenic animals comprise an expression cassette comprising a CNS-1 sequence operably linked to a promoter which controls transcription of a heterologous coding sequence. In another example, the transgenic animals comprise an expression cassette comprising an IL-4 gene, an IL-13 gene and a CNS-1 sequence. In another example, the transgenic animals comprise an expression cassette comprising an IL-4 gene, an IL-13 gene, and a CNS-1 sequence flanked between two recombination site sequences, such as loxP sites. In another embodiment, "knockout" transgenic animals with a deletion of one or more CNS sequences in their chromosomes are made.

The methods for obtaining transgenic animals are well known to those skill in the art. Methods for obtaining transgenic animals are described in, for example, Puhler, A., Ed., Genetic Engineering of Animals, VCH Publ., 1993; Murphy and Carter, Eds., *Transgenesis Techniques: Principles and Protocols* (*Methods in Molecular Biology, Vol. 18*), 1993; and Pinkert, CA, Ed., *Transgenic Animal Technology*: A Laboratory Handbook, Academic Press, 1994. The methods are useful for producing transgenic and chimeric animals of most vertebrate species. Such species include, but are not limited to, nonhuman mammals, including rodents such as mice and rats, rabbits, dogs, cows, sheep and pigs.

Generally, there are two methods for obtaining transgenic animals. In one method, DNA is integrated randomly by injecting it into the pronucleus of a fertilized ovum. In this case, the DNA can integrate anywhere in the genome, and multiple copies often integrate. There is no need for homology between the injected DNA and the host genome. Fertilized oocytes are then cultured in vitro until a pre-implantation embryo is obtained. If desired, the presence of a desired exogenous polynucleotide in the embryo cells can be detected by methods known to those of skill in the art. Methods for culturing fertilized oocytes to the pre-implantation stage are described by Gordon et al., *Methods Enzymol.* 101: 414 (1984); Hogan et al., *Manipulation of the Mouse Embryo: A Laboratory Manual*, C.S.H.L. N.Y. (1986) (mouse embryo); Hammer et al, *Nature* 315: 680 (1985) (rabbit and porcine embryos); Gandolfi et al., *J. Reprod. Fert.* 81: 23–28 (1987); Rexroad et al.,*J. Anim. Sci.* 66: 947–953 (1988) (ovine embryos); and Eyestone et al.,*J. Reprod. Fert.* 85: 715–720 (1989); Camous et al.,*J. Reprod. Fert.* 72: 779–785 (1984); and Heyman et al., *Theriogenology* 27: 5968 (1987) (bovine embryos). Sometimes pre-implantation embryos are stored frozen for a period pending implantation. Pre-implantation embryos are transferred to an appropriate female resulting in the birth of a transgenic or chimeric (for knockout only) animal depending upon the stage of development when the transgene is integrated. Chimeric mammals can be bred to form true germline transgenic animals.

In another method, targeted insertion is used to produce transgenic (knockout animals) animals. In this method, the DNA is introduced into embryonic stem (ES) cells. These cells are obtained from preimplantation embryos cultured in vitro. See, e.g., Hooper, ML, *Embryonal Stem Cells: Introducing Planned Changes into the Animal Germline* (*Modern Genetics, v.* 1), Int'l. Pub. Distrib., Inc., 1993; Bradley et al., *Nature* 309, 255–258 (1984). Cells in which the DNA has undergone homologous recombination with matching genomic sequences are selected. Transformed ES cells are combined with blastocysts from a non-human animal. The ES cells colonize the embryo and in some embryos form the germ line of the resulting chimeric animal. See Jaenisch, *Science* 240: 1468–1474 (1988). Alternatively, ES cells or somatic cells that can reconstitute an organism ("somatic repopulating cells") can be used as a source of nuclei for transplantation into an enucleated fertilized oocyte giving rise to a transgenic animal. See, e.g., Wilmut et al., *Nature* 385: 810–813 (1997).

Any of the above or other methods known in the art can be used to make non-human transgenic animals comprising expression cassettes of the invention. These animals can then be used to further characterize functions of CNS sequences on cytokine genes and to test compounds that modulate regulatory functions of CNS sequences.

VI. Methods for Identifying Compounds that Modulate CNS Sequences

In another aspect, the invention provides methods for identifying compounds that modulate functions of CNS sequences on the cytokine gene expression. Compounds can modulate functions of CNS sequences, e.g., by binding to CNS sequences themselves and/or by interfering with binding of transcription factors to CNS sequences. The effects of compounds on the function of CNS sequences can be assessed using a variety of in vitro and in vivo assays measuring various parameters. These parameters include, e.g., cytokine protein or mRNA levels, transcription or repression of a reporter gene, and the like. Such assays can be used to screen for compounds which are activators, inhibitors or modulators of CNS sequences that can be used to modulate cytokine gene expression and immune response.

In one embodiment, the invention provides methods for identifying compounds that modulate binding of transcription factor(s) to a CNS-1 sequence by contacting the compound with a T cell comprising an expression cassette wherein a CNS-1 sequence is operably linked to a promoter which controls transcription of a reporter gene and determining the functional effect of the compound on the CNS-1 sequence. The reporter gene can be, e.g., a chloramphenicol acetyltransferase gene, a firefly luciferase gene, a bacterial luciferase gene, a β-galactosidase gene, an alkaline phosphatase gene, or a gene that encodes fluorescent proteins such as green fluorescent protein (GFP). After treating the T cells with compounds which potentially modulate functions of CNS sequences, the amount of reporter gene transcription, translation, or activity is measured according to standard techniques know to those of skill in the art.

In another embodiment, the invention provides methods for identifying compounds that modulate transcription factors to a CNS-1 sequence by contacting the compound with a T cell comprising an expression cassette comprises an IL-4 gene, an IL-13 gene and a CNS-1 sequence. The effects of test compounds upon the function of CNS sequences can be determined by comparing the level of cytokine genes, such as IL-4, IL-13, or other interleukin protein or mRNA levels in treated samples and control samples. The level of cytokine protein is measured using immunoassays such as Western blotting, ELISA and the like with cytokine specific antibody. The level of cytokine mRNA can be measured using amplification (e.g., PCR, LCR), hybridization assays (e.g., Northern blots), dot blotting, etc. The level of protein or mRNA is detected using directly or indirectly labeled detection agents, e.g., fluorescently, radioactively, or enzymatically labeled nucleic acids or antibodies.

In another embodiment, the effects of test compounds on CNS sequences are measured in vivo. In this assay, test compounds are administered to the transgenic mouse described above. After a suitable length of time, preferably 4–8 weeks, various parameters are measured. For example, the level of cytokine proteins or mRNA can be measured. In another example, immune response (e.g., asthma-associated phenotype; see Symula et al., *Nature Genet.* 23:241 (1999)) can be measured.

Generally, test compounds can be any small chemical compound, proteins, sugar, nucleic acids or lipids. In some embodiments, compounds can be antisense construct of CNS sequences or antibodies that specifically bind to transcription factors of CNS sequences. In a preferred embodiment, compounds are selected from combinatorial chemical or peptide libraries containing a large number of potential therapeutic compounds. The compounds in the libraries are then screened using one or more assays described herein to identify those library members that display a desired characteristic activity. Generally, the compounds to be tested are present in the assay in the range from 0.1 nM to 10 mM.

To determine the functional effect of the test compound on CNS sequences, results obtained from test samples, such as reporter gene activity, are compared to control samples. Control samples (untreated with a test compound) are assigned relative CNS sequence activity value of 100%. Inhibition of CNS sequence is achieved when the CNS sequence activity value relative to the control is about 90% or less (e.g., 10% less than the control), optionally about 50% or less, about 30% or less, or about 10% or less. Activation of CNS sequence is achieved when the CNS activity value relative to the control is about 110% or higher (e.g., 10% more than the control), optionally about 150% or higher, about 200% higher or about 300% or higher.

Preferably, in both in vitro and in vivo assays, the functional effects of the test compounds are also tested in comparable cells that lack a CNS sequence. For example, if assays were performed with T cells comprising an expression cassette comprising an IL-4 gene, an IL-13 gene and a CNS-1 sequence, then parallel assays are preferably performed with T cells comprising the same expression cassette except lacking the CNS-1 sequence. Such parallel assays allow those of skill in the art to determine that any changes in measured parameters (e.g., reporter gene transcription, IL-4 protein, IL-13 protein) seen with test samples treated with a test compound and control samples untreated with a test compound is not due to the effect of the test compound on elements other than CNS sequences.

VII. Diagnostics and Kits

In another aspect, the invention provides methods for detecting CNS sequences in test samples (either wildtype or mutant). For examples, kits are provided that contain CNS sequence specific probes that specifically hybridize to CNS sequences. The methods, kits and assays described herein can be used for diagnosing patients with mutations in CNS sequences.

Nucleic acid assays for the presence of CNS sequences in a sample are known to those of skill in the art. For example, probes or primers specific for CNS sequences can be used to distinguish between samples which contain CNS sequences and samples which lack CNS sequences or which contain mutations in CNS sequences. The primers can be of any suitable length, e.g., about 10 nucleotides, about 20 nucleotides or less, about 30 nucleotides or less, or about 50 nucleotides or less. Specific primers that can be used to detect CNS-1 through CNS-16 sequences are described in the example section below. Techniques such as Southern analysis, dot blots, amplification techniques such as PCR and LCR, and in situ hybridization can be used as assays.

EXAMPLES

The following examples are offered to illustrate, but not to limit the claimed invention. Examples 1–4 are also described in Loots et al., *Science* 288:136–140 (Apr. 17, 2000), which is incorporated herein in its entirety. It is noted that CNS sequences shown in SEQ ID NOS :1 to 32 are more inclusive than CR sequences provided in provisional Application No. 60/183,657. CNS sequences shown in SEQ ID NOs:1 to 32 are analyzed using the same computer program and the same parameters as in identifying 32 CR sequences shown in the provisional application. The only difference between the CNS sequences shown in SEQ ID NOS:1 to 32 and the CR sequences in the provisional application is that in obtaining the CNS sequences shown in SEQ ID NOS:1 to 32, the maximum length identified by the program as the most conserved and the largest contiguous region is obtained.

Example 1

Comparative Analysis of Non-Coding Sequences in the Interleukin Gene Cluster Region A comparative sequence-based strategy was used to find non-coding sequences with the physical properties of LCR elements in the human 5q31 interleukin gene cluster region. Comparative analysis of ~1 Mb of orthologous human (5q31) and mouse (chromosome 11) sequences identified 90 conserved non-coding elements ($\geq$100 bp in length and $\geq$70% identity). Fifteen of the non-coding elements were experimentally characterized, of which 12 were determined to be single copy in the human genome and 10 to be present ($\geq$75% identity) in at least two mammals in addition to humans and mice. The largest non-coding sequence identified (401 bp in length), CNS-1, was conserved both with regard to sequence (~80% identity in mice, humans, cows, dogs, rabbits) and genomic location (in the IL-4–IL-13 intergenic region in the four mammals examined). Functional characterization of this element in YAC transgenic mice, as described in detail below, revealed it to be a potent regulator of IL-4, IL-13 and IL-5 expression. These genes are spread over 120 kb.

To interrogate the ~1 Mb human 5q31 and mouse chromosome 11 syntenic regions for regulatory elements, computational analysis was first performed to determine their degree of conservation with regards to gene content. Human 5q31 sequence (clones: H14, H13, H23, H11, H16, H21, H18, H15, H24, H17, H26, H25, H81, H22, H20, H82) was obtained (http:/www-hgc.lbl.gov/human-pls.html) and assembled into 9 contigs of the following sizes (given in the directionality of centromere to telomere): 380.0 kb, 13.8 kb, 155.3 kb, 106.9 kb, 155.5 kb, 5.4 kb, 8.9 kb, 32.3 kb, and 90.0 kb. Based on the physical map of the region the 8 gaps have estimated sizes of 12 kb, 4 kb, 5 kb, 3 kb, 16 kb, 2 kb, 5 kb, and 5 kb, respectively. Seven mouse chromosome 11 BACs were isolated from Caltech library CitbCJ7 and sequenced in either draft or finished format: (24OC4 (202 kb); 3.5× draft, 111I81 (151 kb); AC005742 finished, 219O10 (204 kb); 5.0× draft, 32119 (131 kb); 4.0× draft, 33O24 (150 kb); 3.5× draft, 54K15 (145 kb); 5.0× draft, 327O23 (185 kb); 4.0× draft).

Database searches combined with GenScan predictions determined that the human 5q31 region codes for 23 putative genes (including 5 cytokines; IL-4, IL-13, IL-5, IL-3 and granulocyte-macrophage colony-stimulating factor (GM-CSF)) and that the order and orientation of 22 of these genes are conserved in mice (FIG. 1). See Frazer et al., *Genome Res* 7:959 (1997). Genscan is a computer program for the prediction of complete gene structures in human genomic DNA. It is described in *J. Mol. Biol.* 268:78–94 (1997).

Specifically, human repetitive elements were masked using RepeatMasker (A. F. A. Smit and P. Green at http://ftp.genome.washington.edu/RM/RepeatMasker.html). Using gapped BLAST searches (default parameters) masked 5q31 sequences were compared with sequences in NCBI databases, GenPept (Release 113) and UniGene (Sep. 30, 1999), and analyzed for potential coding regions using GenScan (Burge & Karlin, *J. Mol Biol* 268:78 (1997). The following fourteen genes in the interval were previously known and localized based on exact GenPept database matches (NCBI numbers are given): Ubiquinone-binding protein (D50369), GDF-9 (NM_005260), KIF3A (AF041853), IL-4 (A00076), IL-13 (U10307), RAD50 (U63139), IL-5 (NM_000879), IRF1 (P10914), OCTN2 (NM_003060), OCTN1 (NM_003059), P4-hydroxylase alpha (II) (NM_004199), GMCSF (P04141), IL-3 (P08700), and Long chain fatty acyl CoA synthetase 2/KIAA0837 (AF099740/AB020644). Four genes were identified based on GenScan predictions, exact EST matches, and their similarities to known proteins, and are referred to as a homolog of the gene to which they had the highest BLASTX score: pMLLT2-homolog (NM_005935), APX-homolog (Q01613), Septin2-homolog (D86957), and Cyclin I-homolog (NM_006835). Of the five genes referred to by their UniGene number one was identified solely on the basis of an exact UniGene match (Hs.70932) and four were identified by exact UniGene matches in conjunction with GenScan predictions and mouse/human conserved sequences (Hs.1 1637, Hs.77114, Hs.13308, Hs.591082). Two database matches were determined to be pseudogenes: the Lim-domain match (X93510) was exact but only to the first 98 out of 1130 nucleotides in the mRNA, the P4-hydroxylase alpha II pseudogene had neither an open reading frame nor an exact matching EST.

The 1 putative human gene that is not present in the syntenic region of mice, Hs.70932, has no associated GenScan predictions and may represent either an RNA gene or the 3' untranslated region (UTR) of a neighboring gene. These analyses demonstrated that the gene content and order in the human 5q31 and mouse chromosome 11 syntenic regions is largely conserved and therefore suggested that cross-species comparison of the non-coding sequence in this genomic interval would likely identify regulatory elements.

The analysis of the non-coding sequence focused on discovering elements with LCR-like features. To identify non-coding elements with these physical properties, the human (5q31) and mouse (chromosome 11) orthologous sequences were compared with each other and the locations and percent identities of the conserved sequences were displayed in a percent identity plot (PIP). Specifically, alignments between the human and mouse genomic sequences were computed with a dynamic programming method, scoring each nucleotide match as 1, each mismatch as −1, and each gap of length k as −6–0.2 k. The PIP displays the human positions and the percent identity of each segment of the alignment between successive gaps that has length at least 40 bp and at least 60% identity.

A total of 245 conserved sequences (≧100 bp and ≧70% identity) were found, of which 155 overlapped with coding sequences (defined as sequences present in mature RNA transcripts) (9). Specifically, sequences present in mature mRNAs were computationally identified either by exact GenPept matches or exact UniGene matches combined with partial GenPept matches and/or GenScan predictions of probability scores ±0.15. Database matches include the 5' and 3' untranslated regions (UTRs) of mRNAs, therefore some of the 155 conserved coding sequences, as defined in this study, are not translated.

The remaining 90 were defined as non-coding (FIG. 1). To prevent the inclusion of RNA and RNA pseudogenes in this set of conserved noncoding sequences, all tRNA and the majority of known snRNA genes were masked in the human 5q31 sequence by RepeatMasker. However, due to fact that computational screens are biased against RNA genes it is a possibility that a fraction of these 90 conserved non-coding elements may actually be transcribed. The 90 conserved non-coding elements were distributed throughout the entire ~1 Mb human 5q31 interval with 46% in introns, 9% within 1 kb of the 5' and 3' ends of an identified transcript, and 45% in intergenic regions >1 kb from any known gene. Many of the non-coding elements are found in clusters, such as in the intergenic region between OCTN1 and P4-hydroxylase alpha (II), suggesting that they may be working cooperatively as a functional unit (FIG. 1). One of the conserved non-coding sequences (CNS), CNS-7, located in the intergenic region between GM-CSF and IL-3 had previously been experimentally identified as an enhancer controlling the co-regulation of these two cytokines (Osborne et al., *J. Immunol.* 155:226 (1995)). This finding supports the choice of the criteria used in this sequence-based approach to identify biologically relevant non-coding sequences.

Fifteen of the CNSs were assessed for their presence in other vertebrates and their copy number in the human genome. Degenerate primer pairs of the elements were used to amplify genomic DNA of other vertebrates, and the resulting products were sequenced. Specifically, alignments of the 15 human/mouse conserved noncoding sequences were inspected and primer pairs were chosen so that the most conserved 70–320 bp region of each CNS was amplified (see Table 1 in FIG. 2). These shorter CNS sequences are missing their flanking sequences shown in, e.g., SEQ ID NO:1–32 which are more degenerate than the highly conserved core. Hence for each CNS, the size of human PCR amplified product given in Table 1 is smaller than the size of the element indicated in FIG. 1.

Genomic DNA was purchased from Clontech Laboratories (catalog nos. dog 6950-1, rabbit 6960-1, rat 6750-1, mouse 6650-1, human 6550-1, porcine 6651-1, bovine 6850-1, chicken 6852-1). *Drosophila melanogaster* and Fugu rubripes genomic DNA was isolated using standard methods. PCR amplifications were performed as follows: 100 ng of genomic DNA from each species was mixed with 200 uM of each deoxyribonucleoside triphosphate, 1 uM of each oligonucleotide primer (5uM for degenerate primers), 5 ul of 10× PCR buffer (Perkin Elmer), and 5 units of AmpliTaq DNA Polymerase (Perkin Elmer) in a 50 ul volume. The samples were amplified using standard PCR reaction conditions in an automated (Perkin Elmer 9700) thermal cycler for a total of 35 cycles with the following primer pairs: CNS1-forward, 5'-TGATTTCTCGGCAGC-CAGGGAGGGCC-3' (SEQ ID NO:39); reverse, 5'-GGT-GCCTGCGTCACCTCTGACCACAC-3' (SEQ ID NO:40); CNS2-forward, 5'-CCTCTCAGCATTTATCTT-GGGC-3' (SEQ ID NO:41); reverse, 5'-AGAGCCATAA-NNGTGTTTGGG-3' (SEQ ID NO:42); CNS3-forward, 5'-CNAGTNGNTCAGGGCNNGATGCCCAGG-3' (SEQ ID NO:43); reverse, 5'-AAGGGNGTCTGNTCNTNCTG-GAGCCTGCC-3' (SEQ ID NO:44); CNS4-forward, 5'-GCATGAAGNATTGNTGGCCC-3' (SEQ ID NO:45); reverse, 5'-CTCTCTGGCNCTGGAACACC-3' (SEQ ID NO:46); CNS5-forward, 5'-ACNGTTTTTNGTGTGCA-GCACT-3' (SEQ ID NO:47); reverse, 5'-ATTCTTTNAA-AACCCCATATC-3' (SEQ ID NO:48); CNS6-forward, 5'-TAGNANAGTGAGGATGTCTG-3' (SEQ ID NO:49); reverse, 5'-AAACCCCAGCNCTGGGCAAACAG-3' (SEQ ID NO:50); CNS8-forward, 5'-AAGTAAACNCT-GNAAAANNTG-3' (SEQ ID NO:51); reverse, 5'-CNC-NNAAGTATACTTTGGAATCC-3' (SEQ ID NO:52); CNS9-forward 5'-TNACTCNCAGTGACTGATNTTTG-3'

(SEQ ID NO:53); reverse, 5'-ATCNCCTCCNNGTNTC-TTTGCAAC-3' (SEQ ID NO:54); CNS10-forward, 5'-CANGATGACTCAGCCAGCACAAG-3' (SEQ ID NO:55); reverse, 5'-CCTNNTCTAGGAAATGGGCT-TGC-3' (SEQ ID NO:56); CNS11-forward, 5'-GGCAAA-NTGTCACAATGTTC-3' (SEQ ID NO:57); reverse, 5'-CTGTCANAGCCACACAGAAG-3' (SEQ ID NO:58); CNS12-forward, 5'-TCCACATTTTCTTNCCTTTG-3' (SEQ ID NO:59); reverse, 5'-GTNTCNCTGCCCTTTG-ATG-3' (SEQ ID NO:60); CNS13-forward, GGNTGAGA-TNCTGGAGGCTC-3' (SEQ ID NO:61); reverse, 5'-GA-GCAGGTCTGACNNGGGTG-3' (SEQ ID NO:62); CNS14-forward, 5'-TTGGCAATTCCCCTGAAA C-3' (SEQ ID NO:63); reverse, 5'-AAGCTKAGYTCTGGC-AGG-3' (SEQ ID NO:64); CNS15-forward, 5'-AAGNNT-GTTGCTANGGTCACTGTG-3' (SEQ ID NO:65); reverse, 5'-GCAGNTGTGGTTTTGAGANGTTCA T-3' (SEQ ID NO:66); CNS16-forward, 5'-CTCCCACATCC-TTGGGAGGG-3' (SEQ ID NO:67); reverse, 5'-CCA-GNAGCCAGGGACACACC-3' (SEQ ID NO:68). Amplified PCR products were analyzed by gel electrophoresis on 3% Nusieve GTG agarose (FMC) gels, extracted using QIAquick Gel Extraction Kits (QIAGEN), and sequenced using Big Dye chemistiy (PE Applied Biosytems).

Ten of the elements were highly conserved in at least two mammals in addition to humans and mice (FIG. 1 and Table 2). Twelve elements appeared unique in the human genome, as determined by low-stringency Southern blot hybridizations. Specifically, human genomic DNA (8 ug) (Clontech, 6550-1) was digested (Pst I, Msp I, Bgl II, Psi I, Taq$^\alpha$I), separated in an 0.8% agarose gel, transferred onto membrane (Hybond N+, Amersham), hybridized at 52° C. overnight in Church Buffer (0.5 M NaHPO$_4$ (pH:72), 1 mM EDTA, 7% SDS, 1% BSA) with the most stringent wash at 58° C. (0.04 M NaHPO$_4$ (pH:7.2), 1 mM EDTA, 1% SDS). Probes were generated by PCR amplification of human genomic DNA using primer-pairs of each CNS element and gel purified (13). A CNS element was defined as single copy if none of the 5 lanes containing DNA (one of each restriction digest) had more than one or two bands (assumed to be a polymorphism).

Of the noncoding sequences examined, about 70% are conserved across mammals and unique in the human genome, features commonly noted in experimentally identified distant regulatory elements (Li et al., *Trends Genet* 15:403 (1999)).

Example 2

Analysis of CNS-1 Sequence in Several Vertebrate Species

The largest conserved non-coding sequence, CNS-1, which is located in the intergenic region between IL-4 and IL-13, was chosen for in-depth functional analysis based on several features that suggest it may have biological activity. CNS-1 demonstrates a high degree of conservation across mammals (~80% identity in mice, humans, cows, dogs, and rabbits) (Table 1) contrasting sharply with the relatively low conservation observed in the coding regions of the flanking genes, IL-4 and IL-13. The position of CNS-1, which is single copy in the human genome, was mapped in dogs and baboons. Specifically, gridded high-density dog and baboon libraries (BACPAC Resources) were screened by hybridization using the above-described CNS-1 probes generated by PCR amplification of dog and human genomic DNA, respectively. Content mapping of 9 dog BACs and 14 baboon BACs for the presence of KIF3A, CNS-2, IL-4, CNS-1, IL-13 and RAD50 by PCR defined the location of CNS-1 to the IL-4–IL-13 region.

In both cases, they were localized to the IL-4–IL-13 intergenic region suggesting that it has been conserved during evolution not only with regards to sequence but also genomic location. Conserved binding sites for transcription factors known to regulate the expression of IL-4 and IL-13 were not found in CNS-1. Specifically, CNS-1 sequences (human, mouse, dog, rat, cow and rabbit) were searched (http://transfac.gbf-braunschweig.de/TRANSFAC/index.html) for consensus binding sites of 4 proteins (NF-AT, c-maf, GATA-3, STAT6) known to regulate IL-4 transcription.

However, it was determined that CNS-1 does overlaps with two ($T_H2$ cell specific) of the eight DNase I hypersensitive sites (HSs) previously localized in the IL-4–IL-13 region (Takemoto et al., *Int. Immunol* 10:1981 (1998); Agarwal & Rao, *Immunity* 9:765 (1998)). These various lines of evidence support CNS-1 as a likely candidate for a long-range regulatory element of the human 5q31 $T_H2$-type cytokines.

Example 3

Transgenic Mice Comprising the Human 5q31 Region with or without CNS-1

The biological properties of CNS-1 were characterized through the creation and analysis of multiple lines of mice bearing a 450-kb human yeast artificial chromosome (YAC) transgene (FIG. 1) (Frazer et al., *Genome Res.* 7:959 (1997)) either containing or lacking the CNS-1 element. To reduce the uncertainties of comparing different founder lines of transgenic mice for phenotypic differences (with regard to effects caused by transgene copy number or site of integration), the function of CNS-1 was examined using Cre-mediated loxP recombination within the YAC transgenes in vivo.

Specifically, YAC A94G6 (450 kb) was retrofitted using pLys2neo vector (gift from Ken Peterson) as described (Lewis et al., *GATA* 9:86 (1992)). The yeast shuttling vector, pRS406.CNS-1.loxP was constructed as follows: A 2.4 kb Sac I fragment containing human CNS-1 was cloned into pRS406 (Stratagene) to generate pRS406.CNS-1. Oligonucleotides, LoxP-Pml I (forward 5'-GTGTAACT-TTCGTATAGCATACATTATACGAAGTTATCAC-3' (SEQ ID NO:69); reverse 5'-GTGATAACTTCGTATAA-TGTATGCTATACGAAGTTACAC (SEQ ID NO:70)) and LoxP-SphI (forward 5'-CTAACTTCGTATAGCATACAT-TATACGAAGTTAGCATG-3' (SEQ ID NQ:71); reverse 5'-CATAACTTCGTATAATGTATCTATTACGTTAGC-ATG-3 (SEQ ID NO:72)), containing LoxP sequences with sticky ends were synthetically synthesized, annealed in vitro, and subcloned into Pml I and Sph I sites of the pRS406.CNS-1 vector, creating pRS406.CNS-1.loxP. This vector was linearized at the PflM I site and the pop-in/pop-out method (Duff et aL, *Gene Therapy* 1:1 (1993)) was used to modify the retrofitted A94G6 YAC. YAC DNA was isolated at a final concentration of ~1 ng/ml and microinjected into fertilized FVB mouse eggs using standard procedures as previously described in Frazer et al., *Genome Res.* 7:495 (1995).

LoxP sites were inserted into the YAC transgene flanking the CNS-1 element and this modified YAC was introduced into the genome of mice (3 separate founder lines were created) (FIG. 3). To delete the CNS-1 element, the human YAC transgenic mice from each of the founder lines were bred with mice expressing a Cre recombinase transgene (Wagner et al, *NAR* 25:4323 (1997)). This resulted in the generation of two lines of transgenic mice derived from each founder line, one with a CNS-1 containing YAC transgene (CNS-1$^{wt}$) and one with a YAC transgene in which the CNS-1 element had been deleted (CNS-1$^{del}$).

The YAC transgenes in the CNS-1$^{wt}$ and CNS-1$^{del}$ mice were examined for genomic structure and copy number to insure the Cre-loxP recombination system did not cause rearrangements other than the deletion of CNS-1. The structure of the IL-4–IL-13 region was confirmed on Southern blots using human specific probe 1 to detect 9.5 kb and 10.8 kb Bgl II fragments in the CNS-1$^{wt}$ and CNS-1$^{del}$ YAC transgenes, respectively (FIG. 3A, B).

Southern blot hybridizations were performed as described except using hybridization and washing temperatures of 65° C. Probes were generated by PCR amplification of human [probe 1 (forward 5'-CAGGTGGCATCTTGGAAACTG-TCC-3' (SEQ ID NO:73), reverse 5'-AGACCTACCTTG-CCAAGGGCTTCC-3' (SEQ ID NO:74);237 bp); probe 2 (forward 5'-CAGGTGGCATCTTGGAAACTGTCC-3' (SEQ ID NO:75), reverse 5'-AGACCTACCTTGCCAA-GGGCTTCC-3' (SEQ ID NO:76);237 bp)] and mouse [probe 3 (forward 5'-GAGTAAGGCAACTCCGCTCAG-3' (SEQ ID NO:77), reverse 5'-CTGGCTGACACTCTTCA-TCCC-3' (SEQ ID NO:78);205 bp)] genomic DNA. For FISH, slides of lymphocytes isolated from 4 to 6 week old F1 transgenics were prepared and hybridized with two human P1's (H23 and H24) (5) as described (Green et al., in *Genome analysis: a laboratory manual* (Cold Spring Harbor Press, New York) 4:303–413 (1999)).

The same probe also hybridized to an 13.1 kb Sph I fragment (which spans the human IL-4 locus) in both the CNS-1$^{wt}$ and CNS-1$^{del}$ YAC transgenes. These data confirm the deletion of CNS-1 was the only rearrangement in the human IL-4/IL-13 region. For YAC copy number analysis, the relative hybridization intensities of probe 2 (human specific) and probe 3 (mouse specific) were compared on Southern blots (FIG. 3C). Probes 2 and 3 hybridized with equal intensity in the CNS-1$^{wt}$ and CNS-1$^{del}$ transgenic mice of lines 1 and 3, indicating that two YACs are present in their genomes. In the line 2 transgenic animals, probe 2 hybridized at ~50% the intensity of probe 3 indicating that a single YAC is present in these mice. YAC transgene copy number was also examined using fluorescent in situ hybridization (FISH). Hybridization patterns of two P1 probes (H23 and H24) on interphase nuclei were consistent with the presence of 2 YACs in the paired CNS-1$^{wt}$ and CNS-1$^{del}$ transgenic animals in lines 1 and 3, supporting the Southern blot data. These analyses indicate that the Cre-mediated recombination did not change the number of YACs present in the transgenic animals in all 3 lines examined. The paired CNS-1$^{wt}$ and CNS-1$^{del}$ transgenic mice generated in this study are therefore identical in every aspect except for the presence or absence of the CNS-1 element.

Example 4

Effects of CNS-1 Sequence on Cytokine Expression

The effect of CNS-1 on the expression of the three human $T_H2$ cell-specific cytokines, IL-4, IL-13 and IL-5, was assessed in the paired CNS-1$^{wt}$ and CNS-1$^{del}$ transgenic lines. Naive CD4+ T helper cells differentiate into either mature $T_H1$ or $T_H2$ cells over multiple cell divisions after initial activation of the T cell receptor (Gett & Hodgkin, *Proc. Natl. Acad. Sci. USA* 95:9488 (1998); Bird et al., *Immunity* 9:229 (1998)). Highly purified naive CD4+ T cells isolated from the spleen and lymph nodes of CNS-1$^{wt}$ and CNS-1$^{del}$ transgenic mice (at 6–8 weeks of age) were stimulated in vitro under conditions that favor development of either $T_H1$ or $T_H2$ cells.

Specifically, naive CD4+ T cells were sorted to >99% purity from spleen and lymph nodes based on small forward- and side-scattering characteristics and CD4+, CD62L$^{hi}$ phenotype. Cells were activated using irradiated antigen presenting cells with monoclonal antibodies against TCRβ and CD28 with IL-2 and, for $T_H1$ conditions, recombinant murine IL-12 and anti-IL-4 antibody, and for $T_H2$ conditions, recombinant murine IL-4.

As described in Fowell et al., *Immunity* 11:399 (1999), at periods from 2–7 days, CD4+ T cells were analyzed using flow cytometry (positive cells were gated as compared to isotype antibody controls and are based on at least 10,000 flow cytometric events.) for expression of the designated murine and human cytokines by intracellular cytokine detection after 4 hrs of re-stimulation with phorbol myristate acetate and ionomycin (PMA/IONO) (See Symula et al., *Nature Genet*. 23:241 (1999)). Supernatants from activated T cells were collected (either 72 hrs after the primary stimulation with antibodies and irradiated APC, or 24 hrs after re-stimulation of 7 day-old cultures with PMA/IONO) and analyzed using ELISA for human IL-5 and murine IL-13.

Neither the IL-4 nor IL-13 human transgenes were expressed during $T_H1$ differentiation in either the CNS-1$^{wt}$ or CNS-1$^{del}$ transgenic cells, suggesting that CNS-1 is not required for the repression of these cytokines in $T_H1$ cells.

Figure 4:
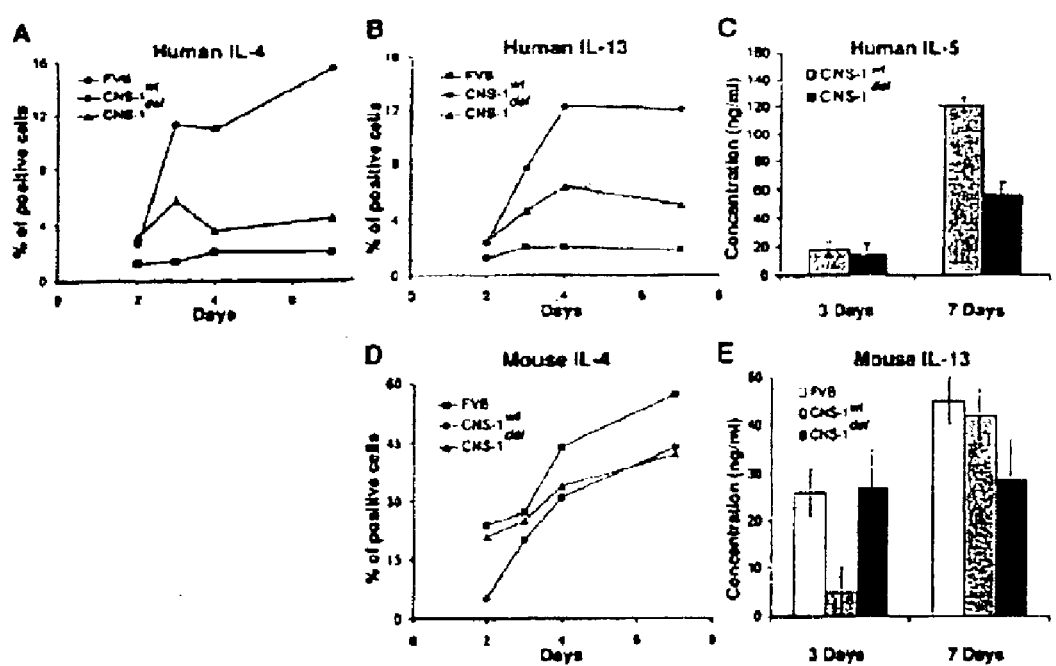
FIGS. 4A–E illustrate expression of human and mouse cytokines in paired CNS-1$^{wt}$ and CNS-1$^{del}$ transgenic and control FVB mice. Naive CD4+ T cells were stimulated using $T_H2$ conditions and analyzed on days 2, 3, 4 and 7 for expression of human IL-4 (A), human IL-13 (C) and murine IL-4 (D) by intracellular cytokine detection using fluorescent monoclonal antibodies. Human IL-5 (C) and murine IL-13 (E) protein levels were determined by ELISA using supernatants of activated T cells collected either 3 days or 7 days (following re-stimulation) after stimulation of naive cells. Bars represent means and standard errors of the means.

Conversely, each of the three human cytokines was appropriately expressed during $T_H2$ differentiation. The effect of CNS-1 was apparent by comparing the number of CNS-1$^{wt}$ and CNS-1$^{del}$ transgenic cells expressing the human cytokines after T cell stimulation (FIG. 4). These analyses indicate that the CNS-1$^{del}$ transgenic cells developed less than half as many human IL-4 producing cells and less than a third as many human IL-13 producing cells as the CNS-1$^{wt}$ transgenic mice. However, in the $T_H2$ cells that express human IL-4 and IL-13, the amounts produced per cell, as assessed by the mean fluorescence intensity, are the same in the paired human CNS-1$^{wt}$ and CNS-1$^{del}$ YAC transgenics.

Production of human IL-5 was also significantly reduced in the CNS-1del transgenic cells as compared with the paired CNS-1$^{wt}$ transgenic cells (FIG. 4C). The reduced expression of human IL-5 could reflect either a decrease in the number of cells producing it, or a decrease in the amounts produced by individual $T_H2$ cells, but the lack of suitable antibodies for flow cytometry precluded us from distinguishing between these two possibilities. All 3 pairs of CNS-1$^{wt}$ and CNS-1$^{del}$ YAC transgenic lines were examined and had consistent results. Human IL-4, IL-13 and IL-5 mRNA levels were quantified in the paired CNS-1$^{wt}$ and CNS-1$^{del}$ transgenic $T_H2$ cells and had the same relative differences as the proteins (data not shown), suggesting that CSN-1 is involved in coordinately regulating the transcriptional activity of these genes.

In the above experiments, total RNA was isolated using RNA-STAT-60 (TEL-TEST"B"). 5 µg of RNA was reverse transcribed into cDNA (Gibco, Superscript II) and expression levels were measured using TaqMan Syber-Green quantitative polymerase chain reaction (PCR) assay (Perkin Elmer).

The sequences of the TaqMan primer pairs (used to quantify mRNA are as follows: hIL-4-forward 5'-ACAG-CCTCACAGAGCAGAAGACT-3' (SEQ ID NO:79) and reverse 5'-GTGTfCTTGGAGGCAGCAAAG-3' (SEQ ID NO:80); hIL-5-forward 5'-ATAAAAATCACCAACTGTG-CACTGAA-3' (SEQ ID NO:81) and reverse 5'-CAAGT-TfTTGAATAGTCTTTCCACAGTAC-3' (SEQ ID NO:82); hIL-13-forward 5'-CAGAAGCTCCGCTCTGCAAT-3' (SEQ ID NO:83) and reverse 5'-ACACGTTGATCAGG-GATTCCA-3' (SEQ ID NQ:84); hKIF3A -forward 5'-CG-CAGTCTCGAGAGCGTCAA-3' (SEQ ID NO:85) and reverse 5'-ACACCGOGTGCGCAGA-3' (SEQ ID NO:86); hRAD50-forward 5'-TGTTGGCTGGCAGGATCTTT-3' (SEQ ID NO:87) and reverse 5'-CGTGAGACCCGCGA-ATCT-3' (SEQ ID NO:88); mGAPDH-forward 5'-GGCA-AATTCAACGGCACAGT-3' (SEQ ID NO:89) and re- verse 5'-CCTCACCCCATTTGATGTTAGTG-3' (SEQ ID NO:90).

To ascertain whether CNS-1 specifically affects the expression of cytokines present on the human 5q31 YAC transgene, RNA isolated from multiple tissues of paired CNS-1$^{wt}$ and CNS-1$^{del}$ transgenic mice was assayed for expression levels of human KIF3A and RAD50 (FIG. 1). The human KIF3A and RAD50 RNA levels were essentially the same in $T_H2$ cells, brains, hearts, kidneys and livers of the paired CNS-1$^{wt}$ and CNS-1$^{del}$ transgenic mice, indicating that their expression in these tissues is not effected by the presence or absence of CNS-1 (data not shown). RAD50 is a large gene (spanning 87 kb) located between IL-13 and IL-5. The fact that the CNS-1$^{del}$ transgenic mice produce significantly less human IL-13 and IL-5 but unaltered amounts of RAD50, therefore suggests that CNS-1 acts over large genomic intervals to specifically affect the expression of $T_H2$ cell-specific cytokines.

The presence of the human CNS-1$^{wt}$ YAC transgene has a prominent effect on the expression levels of the endogenous murine IL-4 and IL-13. Examining this effect provided clues as to how CNS-1 might mechanistically act to influence cytokine expression. In two independent founder lines, the initial production of murine IL-4 and IL-13 was significantly less in CNS-1$^{wt}$ transgenic $T_H2$ cells, while at later time points, CNS-1$^{wt}$ and CNS-1$^{del}$ transgenic $T_H2$ cells expressed comparable amounts of these cytokines (FIG. 4D, 4E). It has been determined that human IL-4 and IL-13 do not modulate murine $T_H2$ cell development in vitro, as assessed using CD4+ T cells from non-transgenic mice (data not shown). These data indicate that the initial reduction in murine IL-4 and IL-13 production in the CNS-1$^{wt}$ transgenic cells is probably not due to the expression of the human IL-4 and IL-13 transgenes, and therefore suggest that a competitive interaction may exist between the human CNS-1 element and a trans-acting murine factor(s). The observation that at subsequent time points the murine cytokines are expressed at equivalent levels in CNS-1$^{wt}$ and CNS-1$^{del}$ transgenic cells may be due either to alterations in the levels of such putative trans-factor(s) with increasing cell division, or to preferential expansion/survival of murine IL-4 and IL-13 producing cells.

Employing a cross-species comparative sequence-based strategy CNS-1 is identified as a regulatory element that acts over a large genomic interval to coordinate the expression of three $T_H2$-type cytokines, IL-4, IL-13 and IL-5. Characterization of this element has revealed that it influences the number of $T_H2$ cells expressing IL-4 and IL-13 but not their levels of expression per cell or the cell types in which they are expressed. These data suggest that CNS-1 increases the likelihood that the human 5q31 $T_H2$ cytokines will be expressed, but does not act as a classical silencer or enhancer, and therefore may be involved in modulating chromatin structure. As shown above, CNS-1 affects the expression of some but not all the genes in a 120 kb interval on human 5q31.

Example 5

CNS-1 Knock-Out Transgenic Mice

A vector containing a neomycin cassette flanked by loxP sites and genomic sequences from the IL-4–IL-13 intergenic region was electroporated into ES cells, and transformants were selected based on resistance to neo-mycin. The recombination event replaced 500 bp of the mouse CNS-1 sequence with the neomycin cassette. This heterozygous knockout cell line was used to generate chimeric mice. The chimeric mice were bred to homozygosity and consequently bred to cre-recombinase mice to remove the neo-mycin cassette as well. The final mouse was homozygous for a 500 bp deletion spanning the whole CNS-1 mouse element.

Example 6

Effects of CNS-2 Sequence on Cytokine Expression

Mouse CNS-2 sequence was cloned upstream of the SV40 and IL-4 promoters in pSEAP expression vectors. Various combinations of the promoters, CNS-2 and the SV40 enhancer were used to analyze the expression of secreted alkaline phosphatase in EL4 cells. Transfection data suggested that CNS-2 acts as a classical enhancer stimulating the IL-4 promoter as well as the SV40 promoter in EL4 cells.

It is understood that the examples and embodiments described herein are for illustrative purposes only and that various modifications or changes in light thereof will be suggested to persons skilled in the art and are to be included within the spirit and purview of this application and scope of the appended claims. While many of the above descriptions are based on CNS-1 sequences, embodiments of the invention are not limited to CNS-1 sequences and their use. Other CNS sequences (i.e., CNS-2 through CNS-16 and CNS-18 through CNS-32) can be used in substantially the same manner as described for CNS-1 sequences.

All publications, patents, and patent applications cited herein are hereby incorporated by reference in their entirety for all purposes.

What is claimed is:

1. An isolated nucleic acid molecule having a length of about 1000 nucleotides or less and comprising a long-range cis-acting regulatory element of the intergenic region between IL-13 and IL-4, wherein the nucleic acid has a sequence at least 80% identical to a sequence of SEQ ID NO:1 and its flanking sequences within the intergenic region between IL-13 and IL-4, or a complement thereof.

2. The isolated nucleic acid molecule of claim 1, wherein the nucleic acid sequence is at least 90% identical to a sequence of SEQ ID NO:1 and its flanking sequences within the intergenic region between IL-13 and IL-4 or a complement thereof.

3. The isolated nucleic acid molecule of claim 1, wherein the nucleic acid sequence is identical to a sequence of SEQ ID NO:1 or a complement thereof.

4. An expression cassette comprising a long-range cis acting regulatory element wherein said long-range cis acting regulatory element is operably linked to a promoter which controls transcription of a heterologous coding sequence and said long-range cis acting regulatory element has a sequence of about 445 nucleotides or less in length which is at least 80% identical to a sequence of SEQ ID NO:1.

5. The expression cassette of claim 4, wherein the long-range cis acting regulatory element has a sequence identical to SEQ ID NO:1.

6. The expression cassette of claim 5, wherein the long-range cis acting regulatory element is located within one kilobase from the promoter.

7. The expression cassette of claim 5, wherein the long-range cis acting regulatory element is located within 100 nucleotides from the promoter.

8. The expression cassette of claim 5, wherein the promoter is a human IL-4 gene promoter or a human IL-13 gene promoter.

9. The expression cassette of claim 4, wherein the heterologous coding sequence is a reporter gene selected from the group consisting of a chloramphenicol acetyltransferase gene, a firefly luciferase gene, a bacterial luciferase gene, a β-galactosidase gene, an alkaline phosphatase gene, or a green fluorescent protein gene.

10. An expression cassette consisting essentially of an IL-4 gene, an IL-13 gene and a long-range cis acting regulatory element, wherein the long-range cis acting regulatory element has a sequence at least 80% identical to the sequence of SEQ ID NO:1.

11. An expression cassette comprising a first recombination site and a second recombination site, an IL-4 gene, an IL-13 gene, and a long-range cis acting regulatory element having at least 80% sequence identity to the sequence of SEQ ID NO:1, wherein the IL-4 gene, and the IL-13 gene as a group are flanked at one end by the first recombination site and at the other end by the second recombination site.

12. The expression cassette of claim 11, wherein the long-range cis acting regulatory element comprises sequence of SEQ ID NO:1.

13. An expression cassette comprising an IL-4 gene and an IL-13 gene, said cassette lacking a sequence identical to the sequence of SEQ ID NO:1.

14. The expression cassette of claim 13, wherein the IL-4 gene is human and the IL-13 gene is human.

15. The expression cassette of claim 14, wherein a marker gene is placed between the IL-4 gene and the IL-13.

16. A T cell comprising the expression cassette of claim 4.

17. A T cell comprising the expression cassette of claim 5.

18. The T cell of claim 17, wherein the T cell is a human cell or a mouse cell.

19. The T cell of claim 18, wherein the T cell is stimulated to differentiate into TH1 or TH2 phenotype.

20. The T cell of claim 16, wherein the genome of the T cell has a deletion of the native sequence of SEQ ID NO:1.

21. A T cell comprising the expression cassette of claim 10.

22. A T cell comprising the expression cassette of claim 11.

23. A T cell comprising the expression cassette of claim 5.

24. The isolated nucleic acid molecule of claim 1, wherein the nucleic acid comprises a conserved non-coding sequence of a long-range cis acting regulatory element wherein the conserved non-coding sequence is identical to the native sequence of a mammal.

25. The cassette of claim 4, wherein the conserved non-coding sequence is a native sequence of a mammal.

26. The T cell of claim 16, wherein the conserved non-coding sequence is the native sequence of a mammal.

27. The cassette of claim 4, wherein the conserved non-coding sequence is about 95% or more identical to SEQ ID NO:1.

28. The T cell of claim 16, wherein the conserved non-coding sequence is about 95% or more identical to SEQ ID NO:1.

29. A nucleic acid molecule of claim 1, wherein the nucleic acid molecule is about 400 nucleotides or less in length.

30. A nucleic acid molecule of claim 1, wherein the nucleic acid molecule is about 200 nucleotides or less in length.

31. A cassette of claim 4, wherein the conserved noncoding sequence is about 400 nucleotides or less in length.

32. A cassette of claim 4, wherein the conserved noncoding sequence is about 200 nucleotides or less in length.

33. The isolated nucleic acid of claim 1, wherein the nucleic acid has a length of about 500 nucleotides or less.

34. The isolated nucleic acid of claim 2, wherein the nucleic acid has a length of about 500 nucleotides or less.

35. The isolated nucleic acid molecule of claim 1, wherein the nucleic acid sequence is at least 95% identical to a sequence of SEQ ID NO:1 and its flanking sequences within the intergenic region between IL-13 and IL-4 or a complement thereof.

36. The isolated nucleic acid of claim 35, wherein the nucleic acid has a length of about 500 nucleotides or less.

37. An expression cassette comprising a long-range cis acting regulatory element wherein said element is operably linked to a promoter which controls transcription of a heterologous coding sequence and the regulatory element has a conserved non-coding sequence of about 1000 nucleotides or less in length which is at least 80% identical to a sequence of SEQ ID NO:1 and the flanking sequences thereof in the human intergenic region between the IL-4 gene and the IL-13 gene.

38. A cassette of claim 37, wherein the conserved non-coding sequence is at least 95% identical to the sequence of SEQ ID NO:1.

39. A T cell comprising the expression cassette of claim 37.

40. A T cell comprising the expression cassette of claim 38.

* * * * *